US008241284B2

(12) United States Patent
Dycus et al.

(10) Patent No.: US 8,241,284 B2
(45) Date of Patent: *Aug. 14, 2012

(54) VESSEL SEALER AND DIVIDER WITH NON-CONDUCTIVE STOP MEMBERS

(75) Inventors: Sean T. Dycus, Broomfield, CO (US); Steven Paul Buysse, Longmont, CO (US); Dax D. Brown, Bardstown, KY (US)

(73) Assignee: Covidien AG (CH)

( * ) Notice: Subject to any disclaimer, the term of this patent is extended or adjusted under 35 U.S.C. 154(b) by 869 days.

This patent is subject to a terminal disclaimer.

(21) Appl. No.: 12/348,748

(22) Filed: Jan. 5, 2009

(65) Prior Publication Data

US 2009/0171350 A1 Jul. 2, 2009

Related U.S. Application Data

(63) Continuation of application No. 10/471,818, filed as application No. PCT/US01/11413 on Apr. 6, 2001, now Pat. No. 7,473,253.

(51) Int. Cl.
*A61B 18/18* (2006.01)
(52) U.S. Cl. .......................................... 606/51
(58) Field of Classification Search .............. 606/45–52, 606/170–174, 205–210
See application file for complete search history.

(56) References Cited

U.S. PATENT DOCUMENTS

| 1,586,645 | A | 6/1926 | Bierman |
| 1,813,902 | A | 7/1931 | Bovie |
| 1,822,330 | A | 9/1931 | Ainslie |
| 1,852,542 | A | 4/1932 | Sovatkin |
| 2,002,594 | A | 5/1935 | Wappler et al. |
| 2,011,169 | A | 8/1935 | Wappler |
| 2,031,682 | A | 2/1936 | Wappler et al. |
| 2,054,149 | A | 9/1936 | Wappler |
| 2,176,479 | A | 10/1939 | Willis |
| 2,305,156 | A | 4/1941 | Grubel |
| 2,279,753 | A | 4/1942 | Knopp |
| 2,327,353 | A | 8/1943 | Karle |
| 2,632,661 | A | 8/1948 | Cristofv |
| 2,668,538 | A | 2/1954 | Baker |

(Continued)

FOREIGN PATENT DOCUMENTS

CA         2104423        2/1994

(Continued)

OTHER PUBLICATIONS

U.S. Appl. No. 12/336,970, filed Dec. 17, 2008.

(Continued)

*Primary Examiner* — Kevin T Truong

(57) ABSTRACT

An endoscopic bipolar forceps includes an elongated shaft having opposing jaw members at a distal end thereof. The jaw members are movable relative to one another from a first position wherein the jaw members are disposed in spaced relation relative to one another to a second position wherein the jaw members cooperate to grasp tissue therebetween. The jaws members are connected to a source of electrical energy such that the jaw members are capable of conducting energy through tissue held therebetween to effect a tissue seal. At least one non-conductive and spaced-apart stop member is disposed on an inner-facing surface of the jaw members to regulate the gap distance between the jaw members when tissue is held therebetween. The forceps also includes a longitudinally reciprocating knife which severs the tissue after sealing at a location which is proximate the sealing site.

18 Claims, 6 Drawing Sheets

U.S. PATENT DOCUMENTS

| | | | |
|---|---|---|---|
| 2,796,065 A | 6/1957 | Kapp | |
| 3,073,311 A | 1/1963 | Tibbs et al. | |
| 3,372,288 A | 3/1968 | Wigington | |
| 3,459,187 A | 8/1969 | Pallotta | |
| 3,643,663 A | 2/1972 | Sutter | |
| 3,648,001 A | 3/1972 | Anderson et al. | |
| 3,651,811 A | 3/1972 | Hildebrandt et al. | |
| 3,678,229 A | 7/1972 | Osika | |
| 3,720,896 A | 3/1973 | Beierlein | |
| 3,763,726 A | 10/1973 | Hildebrand | |
| 3,779,918 A | 12/1973 | Ikeda et al. | |
| 3,801,766 A | 4/1974 | Morrison, Jr. | |
| 3,862,630 A | 1/1975 | Balamuth | |
| 3,863,339 A | 2/1975 | Reaney et al. | |
| 3,866,610 A | 2/1975 | Kletschka | |
| 3,911,766 A | 10/1975 | Fridolph et al. | |
| 3,920,021 A | 11/1975 | Hiltebrandt | |
| 3,921,641 A | 11/1975 | Hulka | |
| 3,938,527 A | 2/1976 | Rioux et al. | |
| 3,952,749 A | 4/1976 | Fridolph et al. | |
| 3,970,088 A | 7/1976 | Morrison | |
| 3,987,795 A | 10/1976 | Morrison | |
| 4,005,714 A | 2/1977 | Hiltebrandt | |
| 4,016,881 A | 4/1977 | Rioux et al. | |
| 4,041,952 A | 8/1977 | Morrison, Jr. et al. | |
| 4,043,342 A | 8/1977 | Morrison, Jr. | |
| 4,074,718 A | 2/1978 | Morrison, Jr. | |
| 4,076,028 A | 2/1978 | Simmons | |
| 4,080,820 A | 3/1978 | Allen | |
| 4,088,134 A | 5/1978 | Mazzariello | |
| 4,112,950 A | 9/1978 | Pike | |
| 4,127,222 A | 11/1978 | Adams | |
| 4,128,099 A | 12/1978 | Bauer | |
| 4,165,746 A | 8/1979 | Burgin | |
| 4,187,420 A | 2/1980 | Piber | |
| 4,233,734 A | 11/1980 | Bies | |
| 4,236,470 A | 12/1980 | Stenson | |
| 4,300,564 A | 11/1981 | Furihata | |
| 4,311,145 A | 1/1982 | Esty et al. | |
| D263,020 S | 2/1982 | Rau, III | |
| 4,370,980 A | 2/1983 | Lottick | |
| 4,375,218 A | 3/1983 | DiGeronimo | |
| 4,416,276 A | 11/1983 | Newton et al. | |
| 4,418,692 A | 12/1983 | Guay | |
| 4,443,935 A | 4/1984 | Zamba et al. | |
| 4,452,246 A | 6/1984 | Bader et al. | |
| 4,470,786 A | 9/1984 | Sano et al. | |
| 4,492,231 A | 1/1985 | Auth | |
| 4,493,320 A | 1/1985 | Treat | |
| 4,503,855 A | 3/1985 | Maslanka | |
| 4,506,669 A | 3/1985 | Blake, III | |
| 4,509,518 A | 4/1985 | McGarry et al. | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,624,254 A | 11/1986 | McGarry et al. | |
| 4,655,215 A | 4/1987 | Pike | |
| 4,655,216 A | 4/1987 | Tischer | |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Xoch et al. | |
| 371,664 | 10/1987 | Brannan et al. | |
| 4,733,662 A | 3/1988 | DeSatnick et al. | |
| D295,893 S | 5/1988 | Sharkany et al. | |
| D295,894 S | 5/1988 | Sharkany et al. | |
| 4,754,892 A | 7/1988 | Retief | |
| 4,763,669 A | 8/1988 | Jaeger | |
| 4,827,929 A | 5/1989 | Hodge | |
| 4,829,313 A | 5/1989 | Taggart | |
| 4,846,171 A | 7/1989 | Kauphusman et al. | |
| 4,887,612 A | 12/1989 | Esser et al. | |
| 4,938,761 A | 7/1990 | Ensslin | |
| 4,947,009 A | 8/1990 | Osika et al. | |
| 4,985,030 A | 1/1991 | Melzer et al. | |
| 5,007,908 A | 4/1991 | Rydell | |
| 5,026,370 A | 6/1991 | Lottick | |
| 5,026,371 A | 6/1991 | Rydell et al. | |
| 5,035,695 A | 7/1991 | Weber, Jr. et al. | |
| 5,037,433 A | 8/1991 | Wilk et al. | |
| 5,042,707 A | 8/1991 | Taheri | |
| 5,047,046 A | 9/1991 | Bodoia | |
| 5,078,716 A | 1/1992 | Doll | |
| 5,084,057 A | 1/1992 | Green et al. | |
| 5,085,659 A | 2/1992 | Rydell | |
| 5,099,840 A | 3/1992 | Goble et al. | |
| 5,100,430 A | 3/1992 | Avellanet et al. | |
| 5,108,392 A | 4/1992 | Spingler | |
| 5,112,343 A | 5/1992 | Thornton | |
| 5,116,332 A | 5/1992 | Lottick | |
| 5,147,357 A | 9/1992 | Rose et al. | |
| 5,151,102 A | 9/1992 | Kamiyama et al. | |
| 5,151,978 A | 9/1992 | Bronikowski et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,209,747 A | 5/1993 | Knoepfler | |
| 5,211,655 A | 5/1993 | Hasson | |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,219,354 A | 6/1993 | Choudhury et al. | |
| 5,244,462 A | 9/1993 | Delahuerga et al. | |
| 5,250,047 A | 10/1993 | Rydell | |
| 5,250,063 A | 10/1993 | Abidin et al. | |
| 5,258,001 A | 11/1993 | Corman | |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A | 2/1994 | Rydell | |
| 5,282,800 A | 2/1994 | Foshee et al. | |
| 5,282,826 A | 2/1994 | Quadri | |
| 5,290,286 A | 3/1994 | Parins | |
| 5,300,082 A | 4/1994 | Sharpe et al. | |
| 5,304,203 A | 4/1994 | El-Mallawany et al. | |
| 5,308,353 A | 5/1994 | Beurrier | |
| 5,308,357 A | 5/1994 | Lichtman | |
| 5,312,433 A | 5/1994 | Boebel et al. | |
| 5,313,027 A | 5/1994 | Inoue et al. | |
| 5,314,445 A | 5/1994 | Degwitz et al. | |
| 5,318,589 A | 6/1994 | Lichtman | |
| 5,324,289 A | 6/1994 | Eggers | |
| D348,930 S | 7/1994 | Olson | |
| 5,326,806 A | 7/1994 | Yokoshima et al. | |
| 5,330,471 A | 7/1994 | Eggers | |
| 5,330,502 A | 7/1994 | Hassler et al. | |
| 5,334,183 A | 8/1994 | Wuchinich | |
| 5,334,215 A | 8/1994 | Chen | |
| 5,336,220 A | 8/1994 | Ryan et al. | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,344,424 A | 9/1994 | Roberts et al. | |
| 5,350,391 A | 9/1994 | Iacovelli | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,368,600 A | 11/1994 | Failla et al. | |
| 5,374,277 A | 12/1994 | Hassler | |
| 5,376,089 A | 12/1994 | Smith | |
| 5,383,875 A | 1/1995 | Bays et al. | |
| 5,383,897 A | 1/1995 | Wholey | |
| 5,389,098 A | 2/1995 | Tsuruta et al. | |
| 5,389,103 A | 2/1995 | Melzer et al. | |
| 5,389,104 A | 2/1995 | Hahnen et al. | |
| 5,391,166 A | 2/1995 | Eggers | |
| 5,391,183 A | 2/1995 | Janzen et al. | |
| 5,396,900 A | 3/1995 | Slater et al. | |
| 5,403,312 A | 4/1995 | Yates et al. | |
| 5,403,342 A | 4/1995 | Tovey et al. | |
| 5,405,344 A | 4/1995 | Williamson et al. | |

| | | | | | | |
|---|---|---|---|---|---|---|
| 5,409,763 A | 4/1995 | Serizawa et al. | | 5,603,711 A | 2/1997 | Parins et al. |
| 5,411,519 A | 5/1995 | Tovey et al. | | 5,603,723 A | 2/1997 | Aranyi et al. |
| 5,411,520 A | 5/1995 | Nash et al. | | 5,611,798 A | 3/1997 | Eggers |
| 5,413,571 A | 5/1995 | Katsaros et al. | | 5,611,808 A | 3/1997 | Hossain et al. |
| 5,415,656 A | 5/1995 | Tihon et al. | | 5,611,813 A | 3/1997 | Lichtman |
| 5,415,657 A | 5/1995 | Taymor-Luria | | 5,620,415 A | 4/1997 | Lucey et al. |
| 5,422,567 A | 6/1995 | Matsunaga | | 5,620,453 A | 4/1997 | Nallakrishnan |
| 5,423,810 A | 6/1995 | Goble et al. | | 5,620,459 A | 4/1997 | Lichtman |
| 5,425,690 A | 6/1995 | Chang | | 5,624,452 A | 4/1997 | Yates |
| 5,425,739 A | 6/1995 | Jessen | | 5,626,578 A | 5/1997 | Tihon |
| 5,429,616 A | 7/1995 | Schaffer | | 5,626,609 A | 5/1997 | Zvenyatsky et al. |
| 5,431,672 A | 7/1995 | Cote et al. | | 5,630,833 A | 5/1997 | Katsaros et al. |
| 5,431,674 A | 7/1995 | Basile et al. | | 5,637,110 A | 6/1997 | Pennybacker et al. |
| 5,437,292 A | 8/1995 | Kipshidze et al. | | 5,638,003 A | 6/1997 | Hall |
| 5,438,302 A | 8/1995 | Goble | | 5,643,294 A | 7/1997 | Tovey et al. |
| 5,439,478 A | 8/1995 | Palmer | | 5,647,869 A | 7/1997 | Goble et al. |
| 5,441,517 A | 8/1995 | Kensey et al. | | 5,647,871 A | 7/1997 | Levine et al. |
| 5,443,463 A | 8/1995 | Stern et al. | | 5,649,959 A | 7/1997 | Hannam et al. |
| 5,443,464 A | 8/1995 | Russell et al. | | 5,655,650 A | 8/1997 | Naitou |
| 5,443,480 A | 8/1995 | Jacobs et al. | | 5,658,281 A | 8/1997 | Heard |
| 5,445,638 A | 8/1995 | Rydell et al. | | D384,413 S | 9/1997 | Zlock et al. |
| 5,445,658 A | 8/1995 | Durrfeld et al. | | 5,662,667 A | 9/1997 | Knodel |
| 5,449,480 A | 9/1995 | Kuriya et al. | | 5,665,100 A | 9/1997 | Yoon |
| 5,451,224 A | 9/1995 | Goble et al. | | 5,667,526 A | 9/1997 | Levin |
| 5,454,823 A | 10/1995 | Richardson et al. | | 5,674,220 A | 10/1997 | Fox et al. |
| 5,454,827 A | 10/1995 | Aust et al. | | 5,674,229 A | 10/1997 | Tovey et al. |
| 5,456,684 A | 10/1995 | Schmidt et al. | | 5,681,282 A | 10/1997 | Eggers et al. |
| 5,458,598 A | 10/1995 | Feinberg et al. | | 5,688,270 A | 11/1997 | Yates et al. |
| 5,460,629 A | 10/1995 | Shlain et al. | | 5,690,652 A | 11/1997 | Wurster et al. |
| 5,461,765 A | 10/1995 | Linden et al. | | 5,690,653 A | 11/1997 | Richardson et al. |
| 5,462,546 A | 10/1995 | Rydell | | 5,693,051 A | 12/1997 | Schulze et al. |
| 5,472,442 A | 12/1995 | Klicek | | 5,693,920 A | 12/1997 | Maeda |
| 5,472,443 A | 12/1995 | Cordis et al. | | 5,695,522 A | 12/1997 | LeMaire, III et al. |
| 5,478,351 A | 12/1995 | Meade et al. | | 5,700,261 A | 12/1997 | Brinkerhoff |
| 5,480,406 A | 1/1996 | Nolan et al. | | 5,700,270 A | 12/1997 | Peyser et al. |
| 5,480,409 A | 1/1996 | Riza | | 5,702,390 A | 12/1997 | Austin et al. |
| 5,484,436 A | 1/1996 | Eggers et al. | | 5,707,369 A | 1/1998 | Vaitekunas et al. |
| 5,496,312 A | 3/1996 | Klicek | | 5,709,680 A | 1/1998 | Yates et al. |
| 5,496,317 A | 3/1996 | Goble et al. | | 5,716,366 A | 2/1998 | Yates |
| 5,496,347 A | 3/1996 | Hashiguchi et al. | | 5,720,744 A | 2/1998 | Eggleston et al. |
| 5,499,997 A | 3/1996 | Sharpe et al. | | 5,722,421 A | 3/1998 | Francese et al. |
| 5,509,922 A | 4/1996 | Aranyi et al. | | 5,725,536 A | 3/1998 | Oberlin et al. |
| 5,512,721 A | 4/1996 | Young et al. | | 5,727,428 A | 3/1998 | LeMaire, III et al. |
| 5,514,134 A | 5/1996 | Rydell et al. | | 5,735,848 A | 4/1998 | Yates et al. |
| 5,527,313 A | 6/1996 | Scott et al. | | 5,743,906 A | 4/1998 | Parins et al. |
| 5,528,833 A | 6/1996 | Sakuma | | 5,752,973 A | 5/1998 | Kieturakis |
| 5,529,067 A | 6/1996 | Larsen et al. | | 5,755,717 A | 5/1998 | Yates et al. |
| 5,531,744 A | 7/1996 | Nardella et al. | | 5,759,188 A | 6/1998 | Yoon |
| 5,536,251 A | 7/1996 | Evard et al. | | 5,766,130 A | 6/1998 | Selmonosky |
| 5,540,684 A | 7/1996 | Hassler, Jr. | | 5,766,166 A | 6/1998 | Hooven |
| 5,540,685 A | 7/1996 | Parins et al. | | 5,766,170 A | 6/1998 | Eggers |
| 5,540,706 A | 7/1996 | Aust et al. | | 5,766,196 A | 6/1998 | Griffiths |
| 5,540,715 A | 7/1996 | Katsaros et al. | | 5,769,849 A | 6/1998 | Eggers |
| 5,542,945 A | 8/1996 | Fritzsch | | 5,772,655 A | 6/1998 | Bauer et al. |
| 5,558,671 A | 9/1996 | Yates | | 5,772,670 A | 6/1998 | Brosa |
| 5,558,672 A | 9/1996 | Edwards et al. | | 5,776,128 A | 7/1998 | Eggers |
| 5,562,619 A | 10/1996 | Mirarchi et al. | | 5,776,130 A | 7/1998 | Buysse et al. |
| 5,562,699 A | 10/1996 | Heimberger et al. | | 5,779,646 A | 7/1998 | Koblish et al. |
| 5,562,720 A | 10/1996 | Stern et al. | | 5,779,701 A | 7/1998 | McBrayer et al. |
| 5,564,615 A | 10/1996 | Bishop et al. | | H1745 H | 8/1998 | Paraschac |
| 5,569,241 A | 10/1996 | Edwardds | | 5,792,137 A | 8/1998 | Carr et al. |
| 5,569,243 A | 10/1996 | Kortenbach et al. | | 5,792,165 A | 8/1998 | Klieman et al. |
| 5,571,100 A | 11/1996 | Goble et al. | | 5,792,177 A | 8/1998 | Kaseda |
| 5,573,424 A | 11/1996 | Poppe | | 5,797,537 A | 8/1998 | Oberlin et al. |
| 5,573,534 A | 11/1996 | Stone | | 5,797,927 A | 8/1998 | Yoon |
| 5,573,535 A | 11/1996 | Viklund | | 5,797,938 A | 8/1998 | Paraschac et al. |
| 5,575,799 A | 11/1996 | Bolanos et al. | | 5,797,941 A | 8/1998 | Schulze et al. |
| 5,575,805 A | 11/1996 | Li | | 5,797,958 A | 8/1998 | Yoon |
| 5,578,052 A | 11/1996 | Koros et al. | | 5,800,449 A | 9/1998 | Wales |
| 5,579,781 A | 12/1996 | Cooke | | 5,807,393 A | 9/1998 | Williamson, IV et al. |
| 5,582,611 A | 12/1996 | Tsukagoshi et al. | | 5,810,764 A | 9/1998 | Eggers et al. |
| 5,582,617 A | 12/1996 | Klieman et al. | | 5,810,805 A | 9/1998 | Sutcu et al. |
| 5,585,896 A | 12/1996 | Yamazaki et al. | | 5,810,808 A | 9/1998 | Eggers |
| 5,590,570 A | 1/1997 | LeMaire, III et al. | | 5,810,811 A | 9/1998 | Yates et al. |
| 5,591,181 A | 1/1997 | Stone et al. | | 5,810,877 A | 9/1998 | Roth et al. |
| 5,597,107 A | 1/1997 | Knodel et al. | | 5,814,043 A | 9/1998 | Shapeton |
| 5,601,224 A | 2/1997 | Bishop et al. | | 5,814,054 A | 9/1998 | Kortenbach et al. |
| 5,601,601 A | 2/1997 | Tal et al. | | 5,817,083 A | 10/1998 | Shemesh et al. |
| 5,601,641 A | 2/1997 | Stephens | | 5,817,119 A | 10/1998 | Klieman et al. |

| | | | | | | |
|---|---|---|---|---|---|---|
| 5,820,630 | A | 10/1998 | Lind | 6,086,601 | A | 7/2000 | Yoon |
| 5,824,978 | A | 10/1998 | Karasik et al. | 6,090,107 | A | 7/2000 | Borgmeier et al. |
| 5,827,271 | A | 10/1998 | Buysse et al. | 6,096,037 | A | 8/2000 | Mulier et al. |
| 5,827,279 | A | 10/1998 | Hughett et al. | 6,099,550 | A | 8/2000 | Yoon |
| 5,827,281 | A | 10/1998 | Levin | 6,102,909 | A | 8/2000 | Chen et al. |
| 5,827,323 | A | 10/1998 | Klieman et al. | 6,106,542 | A | 8/2000 | Toybin et al. |
| 5,827,548 | A | 10/1998 | Lavallee et al. | 6,110,171 | A | 8/2000 | Rydell |
| 5,833,690 | A | 11/1998 | Yates et al. | 6,113,596 | A | 9/2000 | Hooven et al. |
| 5,843,080 | A | 12/1998 | Fleenor et al. | 6,113,598 | A | 9/2000 | Baker |
| 5,849,022 | A | 12/1998 | Sakashita et al. | 6,117,158 | A | 9/2000 | Measamer et al. |
| 5,853,412 | A | 12/1998 | Mayenberger | 6,122,549 | A | 9/2000 | Sharkey et al. |
| 5,859,527 | A | 1/1999 | Cook | 6,123,701 | A | 9/2000 | Nezhat |
| 5,860,976 | A | 1/1999 | Billings et al. | H1904 | H | 10/2000 | Yates et al. |
| 5,876,401 | A | 3/1999 | Schulze et al. | 6,126,658 | A | 10/2000 | Baker |
| 5,876,412 | A | 3/1999 | Piraka | 6,126,665 | A | 10/2000 | Yoon |
| 5,882,567 | A | 3/1999 | Cavallaro et al. | 6,139,563 | A | 10/2000 | Cosgrove, III et al. |
| 5,891,141 | A | 4/1999 | Rydell | 6,143,005 | A | 11/2000 | Yoon et al. |
| 5,891,142 | A | 4/1999 | Eggers et al. | 6,152,923 | A | 11/2000 | Ryan |
| 5,893,863 | A | 4/1999 | Yoon | 6,162,220 | A | 12/2000 | Nezhat |
| 5,893,875 | A | 4/1999 | O'Connor et al. | 6,171,316 | B1 | 1/2001 | Kovac et al. |
| 5,893,877 | A | 4/1999 | Gampp, Jr. et al. | 6,174,309 | B1 | 1/2001 | Wrublewski et al. |
| 5,897,563 | A | 4/1999 | Yoon et al. | 6,178,628 | B1 | 1/2001 | Clemens et al. |
| 5,902,301 | A | 5/1999 | Olig | 6,179,834 | B1 | 1/2001 | Buysse et al. |
| 5,906,630 | A | 5/1999 | Anderhub et al. | 6,179,837 | B1 | 1/2001 | Hooven |
| 5,908,420 | A | 6/1999 | Parins et al. | 6,183,467 | B1 | 2/2001 | Shapeton et al. |
| 5,908,432 | A | 6/1999 | Pan | 6,187,003 | B1 | 2/2001 | Buysse et al. |
| 5,911,719 | A | 6/1999 | Eggers | 6,190,386 | B1 | 2/2001 | Rydell |
| 5,913,874 | A | 6/1999 | Berns et al. | 6,190,400 | B1 | 2/2001 | VanDeMoer et al. |
| 5,921,916 | A | 7/1999 | Aeikens et al. | 6,193,718 | B1 | 2/2001 | Kortenbach et al. |
| 5,921,984 | A | 7/1999 | Sutcu et al. | 6,206,876 | B1 | 3/2001 | Levine et al. |
| 5,925,043 | A | 7/1999 | Kumar et al. | 6,206,877 | B1 | 3/2001 | Kese et al. |
| 5,928,136 | A | 7/1999 | Barry | 6,206,893 | B1 | 3/2001 | Klein et al. |
| 5,935,126 | A | 8/1999 | Riza | 6,214,028 | B1 | 4/2001 | Yoon et al. |
| 5,941,869 | A | 8/1999 | Patterson et al. | 6,217,602 | B1 | 4/2001 | Redmon |
| 5,944,718 | A | 8/1999 | Dafforn et al. | 6,217,615 | B1 | 4/2001 | Sioshansi et al. |
| 5,951,546 | A | 9/1999 | Lorentzen | 6,221,039 | B1 | 4/2001 | Durgin et al. |
| 5,951,549 | A | 9/1999 | Richardson et al. | 6,223,100 | B1 | 4/2001 | Green |
| 5,954,720 | A | 9/1999 | Wilson et al. | 6,224,593 | B1 | 5/2001 | Ryan et al. |
| 5,954,731 | A | 9/1999 | Yoon | 6,224,614 | B1 | 5/2001 | Yoon |
| 5,954,733 | A | 9/1999 | Yoon | 6,228,080 | B1 | 5/2001 | Gines |
| 5,957,923 | A | 9/1999 | Hahnen et al. | 6,228,083 | B1 | 5/2001 | Lands et al. |
| 5,957,937 | A | 9/1999 | Yoon | 6,248,124 | B1 | 6/2001 | Pedros et al. |
| 5,960,544 | A | 10/1999 | Beyers | 6,248,944 | B1 | 6/2001 | Ito |
| 5,961,514 | A | 10/1999 | Long et al. | 6,261,307 | B1 | 7/2001 | Yoon et al. |
| 5,964,758 | A | 10/1999 | Dresden | 6,267,761 | B1 | 7/2001 | Ryan |
| 5,976,132 | A | 11/1999 | Morris | 6,270,497 | B1 | 8/2001 | Sekino et al. |
| 5,984,932 | A | 11/1999 | Yoon | 6,270,508 | B1 | 8/2001 | Klieman et al. |
| 5,984,938 | A | 11/1999 | Yoon | 6,273,887 | B1 | 8/2001 | Yamauchi et al. |
| 5,984,939 | A | 11/1999 | Yoon | 6,277,117 | B1 | 8/2001 | Tetzlaff et al. |
| 5,989,277 | A | 11/1999 | LeMaire, III et al. | 6,280,458 | B1 | 8/2001 | Boche et al. |
| 5,993,466 | A | 11/1999 | Yoon | 6,283,961 | B1 | 9/2001 | Underwood et al. |
| 5,993,467 | A | 11/1999 | Yoon | D449,886 | S | 10/2001 | Tetzlaff et al. |
| 5,997,565 | A | 12/1999 | Inoue | 6,298,550 | B1 | 10/2001 | Kirwan |
| 6,004,332 | A | 12/1999 | Yoon et al. | 6,302,424 | B1 | 10/2001 | Gisinger et al. |
| 6,004,335 | A | 12/1999 | Vaitekunas et al. | 6,319,262 | B1 | 11/2001 | Bates et al. |
| 6,010,516 | A | 1/2000 | Hulka et al. | 6,319,451 | B1 | 11/2001 | Brune |
| 6,017,358 | A | 1/2000 | Yoon et al. | 6,322,561 | B1 | 11/2001 | Eggers et al. |
| 6,021,693 | A | 2/2000 | Feng-Sing | 6,322,580 | B1 | 11/2001 | Kanner |
| 6,024,741 | A | 2/2000 | Williamson et al. | 6,325,795 | B1 | 12/2001 | Lindemann et al. |
| 6,024,743 | A | 2/2000 | Edwards | 6,334,860 | B1 | 1/2002 | Dorn |
| 6,024,744 | A | 2/2000 | Kese et al. | 6,334,861 | B1 | 1/2002 | Chandler et al. |
| 6,027,522 | A | 2/2000 | Palmer | 6,345,532 | B1 | 2/2002 | Coudray et al. |
| 6,030,384 | A | 2/2000 | Nezhat | 6,350,264 | B1 | 2/2002 | Hooven |
| 6,033,399 | A | 3/2000 | Gines | 6,352,536 | B1 | 3/2002 | Buysse et al. |
| 6,039,733 | A | 3/2000 | Buysse et al. | 6,358,249 | B1 | 3/2002 | Chen et al. |
| 6,041,679 | A | 3/2000 | Slater et al. | 6,358,259 | B1 | 3/2002 | Swain et al. |
| 6,050,996 | A | 4/2000 | Schmaltz et al. | 6,358,268 | B1 | 3/2002 | Hunt et al. |
| 6,053,914 | A | 4/2000 | Eggers et al. | 6,364,879 | B1 | 4/2002 | Chen et al. |
| 6,053,933 | A | 4/2000 | Balazs et al. | D457,958 | S | 5/2002 | Dycus et al. |
| D424,694 | S | 5/2000 | Tetzlaff et al. | D457,959 | S | 5/2002 | Tetzlaff et al. |
| D425,201 | S | 5/2000 | Tetzlaff et al. | 6,387,094 | B1 | 5/2002 | Eitenmuller |
| 6,059,782 | A | 5/2000 | Novak et al. | 6,391,035 | B1 | 5/2002 | Appleby et al. |
| 6,066,139 | A | 5/2000 | Ryan et al. | 702,472 | A1 | 6/2002 | Pignolet |
| 6,074,386 | A | 6/2000 | Goble et al. | 6,398,779 | B1 | 6/2002 | Buysse et al. |
| 6,077,287 | A | 6/2000 | Taylor et al. | 6,402,747 | B1 | 6/2002 | Lindemann et al. |
| 6,080,180 | A | 6/2000 | Yoon et al. | 6,409,728 | B1 | 6/2002 | Ehr et al. |
| RE36,795 | E | 7/2000 | Rydell | H2037 | H | 7/2002 | Yates et al. |
| 6,083,223 | A | 7/2000 | Baker | 6,419,675 | B1 | 7/2002 | Gallo, Sr. |
| 6,086,586 | A | 7/2000 | Hooven | 6,425,896 | B1 | 7/2002 | Baltschun et al. |

| Patent No. | Date | Inventor(s) |
|---|---|---|
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 728,883 A1 | 5/2003 | Downes |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |

| Patent No. | Date | Inventor |
|---|---|---|
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelton, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jhigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0107517 A1 | 8/2002 | Witt et al. |
| 2002/0111624 A1 | 8/2002 | Witt et al. |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0115296 A1 | 6/2004 | Duffin |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0236326 A1 | 11/2004 | Schulze et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101952 A1 | 5/2005 | Lands et al. |
| 2005/0149017 A1 | 7/2005 | Dycus |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0052778 A1 | 3/2006 | Chapman et al. |
| 2006/0052779 A1 | 3/2006 | Hammill |
| 2006/0064086 A1 | 3/2006 | Odom |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0213708 A1* | 9/2007 | Dumbauld et al. ............. 606/45 |
| 2007/0213712 A1 | 9/2007 | Buysse et al. |
| 2007/0255279 A1 | 11/2007 | Buysse et al. |
| 2007/0260235 A1 | 11/2007 | Podjahsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |

| | | | | | | |
|---|---|---|---|---|---|---|
| 2008/0004616 A1 | 1/2008 | Patrick | | EP | 0878169 | 11/1998 |
| 2008/0009860 A1 | 1/2008 | Odom | | EP | 0887046 | 1/1999 |
| 2008/0015575 A1 | 1/2008 | Odom et al. | | EP | 0923907 | 6/1999 |
| 2008/0021450 A1 | 1/2008 | Couture | | EP | 0640317 | 9/1999 |
| 2008/0033428 A1 | 2/2008 | Artale et al. | | EP | 0986990 | 3/2000 |
| 2008/0039835 A1 | 2/2008 | Johnson et al. | | EP | 1034747 | 9/2000 |
| 2008/0039836 A1 | 2/2008 | Odom et al. | | EP | 1034748 | 9/2000 |
| 2008/0045947 A1 | 2/2008 | Johnson et al. | | EP | 1025807 | 10/2000 |
| 2008/0058802 A1 | 3/2008 | Couture et al. | | EP | 1034746 | 10/2000 |
| 2008/0082100 A1 | 4/2008 | Orton et al. | | EP | 1050278 | 11/2000 |
| 2008/0091189 A1 | 4/2008 | Carlton | | EP | 1053719 | 11/2000 |
| 2008/0195093 A1 | 8/2008 | Couture et al. | | EP | 1053720 | 11/2000 |
| 2008/0215051 A1 | 9/2008 | Buysse et al. | | EP | 1055399 | 11/2000 |
| 2008/0243120 A1 | 10/2008 | Lawes et al. | | EP | 1055400 | 11/2000 |
| 2008/0249527 A1 | 10/2008 | Couture | | EP | 1080694 | 3/2001 |
| 2008/0312653 A1 | 12/2008 | Arts et al. | | EP | 1082944 | 3/2001 |
| 2008/0319442 A1 | 12/2008 | Unger et al. | | EP | 1159926 | 12/2001 |
| 2009/0012520 A1 | 1/2009 | Hixson et al. | | EP | 1177771 | 2/2002 |
| 2009/0018535 A1 | 1/2009 | Schechter et al. | | EP | 1301135 | 4/2003 |
| 2009/0024126 A1 | 1/2009 | Artale et al. | | EP | 1330991 | 7/2003 |
| 2009/0043304 A1 | 2/2009 | Tetzlaff et al. | | EP | 1486177 | 6/2004 |
| 2009/0048596 A1 | 2/2009 | Shields et al. | | EP | 1472984 | 11/2004 |
| 2009/0062794 A1 | 3/2009 | Buysse et al. | | EP | 0774232 | 1/2005 |
| 2009/0082766 A1 | 3/2009 | Unger et al. | | EP | 1527747 | 5/2005 |
| 2009/0082767 A1 | 3/2009 | Unger et al. | | EP | 1530952 | 5/2005 |
| 2009/0082769 A1 | 3/2009 | Unger et al. | | EP | 1532932 | 5/2005 |
| 2009/0088738 A1 | 4/2009 | Guerra et al. | | EP | 1535581 | 6/2005 |
| 2009/0088739 A1 | 4/2009 | Hushka et al. | | EP | 1609430 | 12/2005 |
| 2009/0088740 A1 | 4/2009 | Guerra et al. | | EP | 1632192 | 3/2006 |
| 2009/0088741 A1 | 4/2009 | Hushka et al. | | EP | 1642543 | 4/2006 |
| 2009/0088744 A1 | 4/2009 | Townsend | | EP | 1645238 | 4/2006 |
| 2009/0088745 A1 | 4/2009 | Hushka et al. | | EP | 1645240 | 4/2006 |
| 2009/0088746 A1 | 4/2009 | Hushka et al. | | EP | 1649821 | 4/2006 |
| 2009/0088747 A1 | 4/2009 | Hushka et al. | | EP | 1707143 | 10/2006 |
| 2009/0088748 A1 | 4/2009 | Guerra et al. | | EP | 1769765 | 4/2007 |
| 2009/0088749 A1 | 4/2009 | Hushka et al. | | EP | 1769766 | 4/2007 |
| 2009/0088750 A1 | 4/2009 | Hushka et al. | | EP | 1929970 | 6/2008 |
| 2009/0112206 A1 | 4/2009 | Dumbauld et al. | | EP | 1683496 | 12/2008 |
| 2009/0131934 A1 | 5/2009 | Odom et al. | | GB | 623316 | 5/1949 |
| 2009/0149853 A1 | 6/2009 | Shields et al. | | GB | 1490585 | 11/1977 |
| 2009/0149854 A1 | 6/2009 | Cunningham et al. | | GB | 2214430 A | 6/1989 |
| 2009/0171350 A1 | 7/2009 | Dycus et al. | | GB | 2213416 A | 8/1989 |
| 2009/0171353 A1 | 7/2009 | Johnson et al. | | JP | 61-501068 | 9/1984 |
| 2009/0182327 A1 | 7/2009 | Unger | | JP | 6-502328 | 3/1992 |
| 2009/0187188 A1 | 7/2009 | Guerra et al. | | JP | 5-5106 | 1/1993 |
| 2011/0275901 A1* | 11/2011 | Shelton, IV .................. 606/174 | | JP | 5-40112 | 2/1993 |
| | | | | JP | 06343644 | 12/1994 |
| FOREIGN PATENT DOCUMENTS | | | | JP | 07265328 | 10/1995 |
| DE | 2415263 | 10/1975 | | JP | 08056955 | 3/1996 |
| DE | 2514501 | 10/1976 | | JP | 08252263 | 10/1996 |
| DE | 2627679 | 1/1977 | | JP | 09010223 | 1/1997 |
| DE | 3612646 | 4/1987 | | JP | 11244298 | 9/1999 |
| DE | 8712328 | 3/1988 | | JP | 2000-342599 | 12/2000 |
| DE | 4303882 | 8/1994 | | JP | 2000-350732 | 12/2000 |
| DE | 4403252 | 8/1995 | | JP | 2001-008944 | 1/2001 |
| DE | 19515914 | 7/1996 | | JP | 2001-029356 | 2/2001 |
| DE | 29616210 | 1/1997 | | JP | 2001-128990 | 5/2001 |
| DE | 19608716 | 4/1997 | | SU | 401367 | 11/1974 |
| DE | 19751106 | 5/1998 | | WO | WO 89/00757 | 1/1989 |
| DE | 19751108 | 5/1999 | | WO | WO 92/04873 | 4/1992 |
| DE | 19738457 | 1/2009 | | WO | WO 92/06642 | 4/1992 |
| EP | 0364216 | 4/1990 | | WO | WO 93/21845 | 11/1993 |
| EP | 0467501 | 1/1992 | | WO | WO 94/08524 | 4/1994 |
| EP | 0518230 | 12/1992 | | WO | WO 94/20025 | 9/1994 |
| EP | 0541930 | 5/1993 | | WO | WO 95/02369 | 1/1995 |
| EP | 0572131 | 12/1993 | | WO | WO 95/07662 | 3/1995 |
| EP | 0584787 | 3/1994 | | WO | WO 95/15124 | 6/1995 |
| EP | 0589453 | 3/1994 | | WO | WO 96/05776 | 2/1996 |
| EP | 0589555 | 3/1994 | | WO | WO 96/022056 | 7/1996 |
| EP | 0623316 | 11/1994 | | WO | WO 96/13218 | 9/1996 |
| EP | 0624348 | 11/1994 | | WO | WO 97/00646 | 1/1997 |
| EP | 0 640 317 | 3/1995 | | WO | WO 97/00647 | 1/1997 |
| EP | 0650701 | 5/1995 | | WO | WO 97/10764 | 3/1997 |
| EP | 0694290 | 3/1996 | | WO | WO 97/24073 | 7/1997 |
| EP | 0717966 | 6/1996 | | WO | WO 97/24993 | 7/1997 |
| EP | 0754437 | 3/1997 | | WO | WO 98/27880 | 7/1998 |
| EP | 0517243 | 9/1997 | | WO | WO 99/03407 | 1/1999 |
| EP | 0853922 | 7/1998 | | WO | WO 99/03408 | 1/1999 |
| EP | 0875209 | 11/1998 | | WO | WO 99/03409 | 1/1999 |

| | | |
|---|---|---|
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

U.S. Appl. No. 12/399,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing For Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report Ep 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
International Search Report EP06008515.6 Dated Jan. 8, 2009.
Official Action issued by the Canadian Patent Office in co-pending Canadian Patent Application No. 2,442,598 mailed Nov. 3, 2009.
European Search Report dated Aug. 31, 2011 for EP Appln. No. EP 10 16 7655.

* cited by examiner

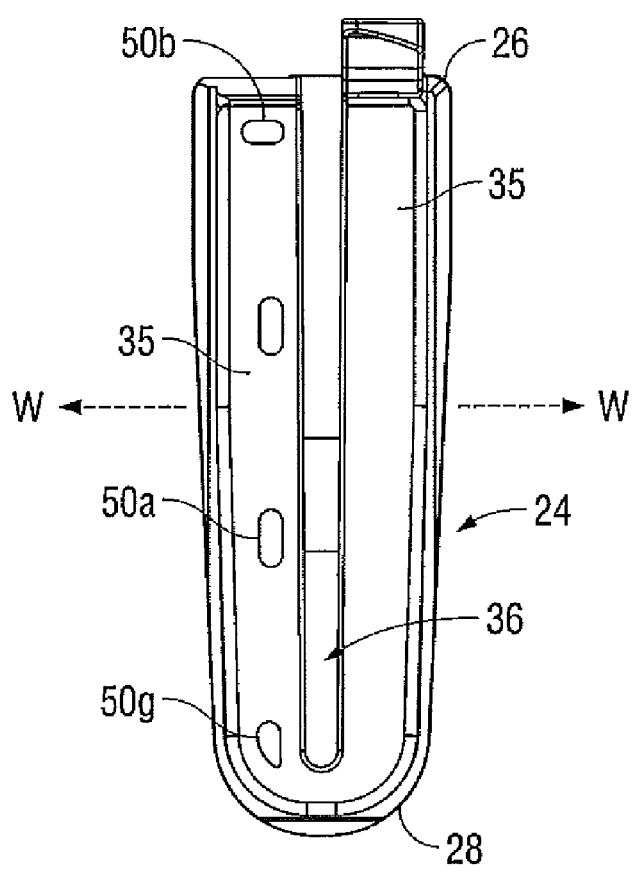 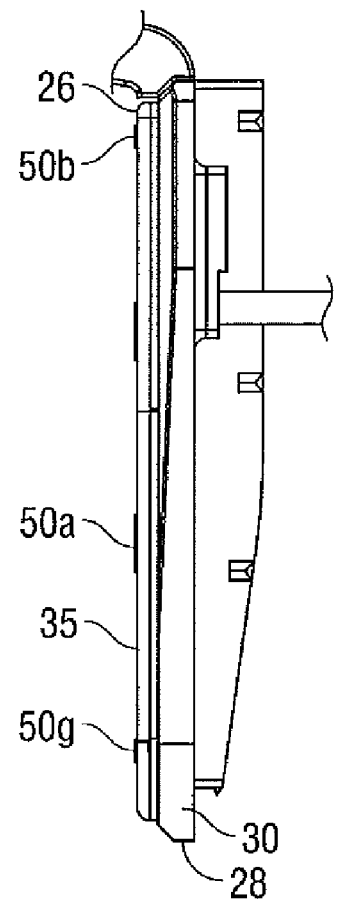
FIG. 6A  FIG. 6B

VESSEL SEALER AND DIVIDER WITH NON-CONDUCTIVE STOP MEMBERS

CROSS-REFERENCE TO RELATED APPLICATIONS

This application is a continuation of U.S. application Ser. No. 10/471,818 filed Sep. 11, 2003 now U.S. Pat. No. 7,473,253 which claims the benefit of and priority to PCT Application Serial No. PCT/US01/11413 filed Apr. 6, 2001 entitled "VESSEL SEALER AND DIVIDER WITH NON-CONDUCTIVE STOP MEMBERS" the entire contents of each of these applications are hereby incorporated by reference.

BACKGROUND

The present disclosure relates to an electrosurgical instrument and method for performing endoscopic surgical procedures. More particularly, the present disclosure relates to an endoscopic bipolar electrosurgical forceps and method of using same which includes a non-conductive stop member associated with one or both of the opposing jaw members. The non-conductive stop member is designed to control the gap distance between opposing jaw members and enhance the manipulation and gripping of tissue during the sealing and dividing process.

TECHNICAL FIELD

Endoscopic forceps utilize mechanical action to constrict, grasp, dissect and/or clamp tissue. Endoscopic electrosurgical forceps utilize both mechanical clamping action and electrical energy to effect hemostasis by heating the tissue and blood vessels to coagulate, cauterize and/or seal tissue.

Endoscopic instruments are inserted into the patient through a cannula, or port, that has been made with a trocar or similar such device. Typical sizes for cannulas range from three millimeters to twelve millimeters. Smaller cannulas are usually preferred, and this presents a design challenge to instrument manufacturers who must find ways to make surgical instruments that fit through the cannulas.

Certain endoscopic surgical procedures require cutting blood vessels or vascular tissue. However, due to space limitations surgeons can have difficulty suturing vessels or performing other traditional methods of controlling bleeding, e.g., clamping and/or tying-off transected blood vessels. Blood vessels, in the range below two millimeters in diameter, can often be closed using standard electrosurgical techniques. However, if a larger vessel is severed, it may be necessary for the surgeon to convert the endoscopic procedure into an open-surgical procedure and thereby abandon the benefits of laparoscopy.

Several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187-190, describes a method for terminating electrosurgical power to the vessel so that charring of the vessel walls can be avoided.

As mentioned above, by utilizing an electrosurgical forceps, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to a different electric potential such that when the jaw members grasp tissue, electrical energy can be selectively transferred through the tissue.

In order to effect a proper seal with larger vessels, two predominant mechanical parameters must be accurately controlled—the pressure applied to the vessel and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.005 inches. Below this range, the seal may shred or tear and above this range the lumens may not be properly or effectively sealed.

Electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, "coagulation" is defined as a process of desiccating tissue wherein the tissue cells are ruptured and dried. Vessel sealing is defined as the process of liquefying the collagen in the tissue so that it reforms into a fused mass. Thus, coagulation of small vessels is sufficient to permanently close them. Larger vessels need to be sealed to assure permanent closure.

U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue. However, some of these designs may not provide uniformly reproducible pressure to the blood vessel and may result in an ineffective or non-uniform seal.

For the most part, these instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting seated tissue by controlling clamping pressure alone for either of two reasons: 1) if too much force is applied, there is a possibility that the two poles will touch and energy will not be transferred through the tissue resulting in an ineffective seal; or 2) if too low a force is applied the tissue may pre-maturely move prior to activation and sealing and/or a thicker, less reliable seat may be created.

Typically and particularly with respect to endoscopic electrosurgical procedures, once a vessel is sealed, the surgeon has to remove the sealing instrument from the operative site, substitute a new instrument through the cannula and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue sealing line.

Several attempts have been made to design an instrument which incorporates a knife or blade member which effectively severs the tissue after forming a tissue seal. For example, U.S. Pat. No. 5,674,220 to Fox et al. discloses a transparent vessel sealing instrument which includes a longitudinally reciprocating knife which severs the tissue once seated. The instrument includes a plurality of openings which enable direct visualization of the tissue during the sealing and severing process. This direct visualization allows a user to visually and manually regulate the closure force and gap distance between jaw members to reduce and/or limit certain undesirable effects known to occur when sealing vessels, thermal spread, charring, etc. As can be appreciated, the overall success of creating a tissue seal with this instrument is greatly reliant upon the user's expertise, vision, dexterity, and experience in judging the appropriate closure force, gap distance and length of reciprocation of the knife to uniformly, consistently and effectively seal the vessel and separate the tissue at the seal.

U.S. Pat. No. 5,702,390 to Austin et al. discloses a vessel sealing instrument which includes a triangularly-shaped electrode which is rotatable from a first position to seal tissue to a second position to cut tissue. Again, the user must rely on direct visualization and expertise to control the various effects of sealing and cutting tissue.

Thus, a need exists to develop an endoscopic electrosurgical instrument which effectively and consistently seals and separates vascular tissue and solves the aforementioned problems. This instrument regulates the gap distances between opposing jaws members, reduces the chances of short circuiting the opposing jaws during activation and assists in manipulating, gripping and holding the tissue prior to and during activation and separation of the tissue.

SUMMARY

The present disclosure relates to an endoscopic bipolar electrosurgical forceps for clamping, sealing and/or dividing tissue. The forceps includes an elongated shaft having opposing jaw members at a distal end thereof. The jaw members are movable relative to one another from a first position wherein the jaw members are disposed in spaced relation relative to one another to a second position wherein the jaw members cooperate to grasp tissue therebetween. An electrosurgical energy source is connected to the jaw members such that the jaw members are capable of conducting energy through tissue held therebetween to effect a tissue seal. At least one non-conductive and spaced-apart stop member is disposed on an inner-facing surface of at least one of the jaw members and is positioned to control the gap distance between the opposing jaw members when the tissue is held therebetween. A longitudinally reciprocating knife severs the tissue proximate the sealing site once an effective seal is formed.

One embodiment of the presently disclosed forceps includes a drive rod assembly which connects the jaw members to the source of electrical energy such that the first jaw member has a first electrical potential and the second jaw member has a second electrical potential. Preferably, a handle mechanically engages the drive rod assembly and imparts movement of the first and second jaw members relative to one another.

In one embodiment of the present disclosure, one of the jaw members includes an electrically conductive surface having a longitudinally-oriented channel defined therein which facilitates longitudinal reciprocation of the knife for severing tissue. Preferably, the forceps includes a trigger for actuating the knife which is independently operable from the drive assembly.

In one embodiment, the forceps includes at least two stop members arranged as a series of longitudinally-oriented projections which extend along the inner-facing surface from the proximal end to the distal end of the jaw member. In another embodiment the stop members include a series of circle-like tabs which project from the inner facing surface and extend from the proximal end to the distal end of the jaw member. The stop members may be disposed on either opposing jaw member on opposite sides of the longitudinally-oriented channel and/or in an alternating, laterally-offset manner relative to one another along the length of the surface of either or both jaw members.

In another embodiment of the present disclosure, a raised lip is provided to act as a stop member which projects from the inner-facing surface and extends about the outer periphery of the jaw member to control the gap distance between opposing jaw members. In another embodiment, at least one longitudinally-oriented ridge extends from the proximal end to the distal end of one of the jaw members and controls the gap distance between the jaw members.

Preferably, the stop members are affixed/attached to the jaw member(s) by stamping, thermal spraying, overmolding and/or by an adhesive. The stop members project from about 0.001 inches to about 0.005 inches and, preferably, from about 0.002 inches to about 0.003 inches from the inner-facing surface of at least one of the jaw members. It is envisioned that the stop members may be made from an insulative material such as parylene, nylon and/or ceramic. Other materials are also contemplated, e.g., syndiotactic polystryrenes such as QUESTRA® manufactured by DOW Chemical, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

Another embodiment of the present disclosure includes an endoscopic bipolar forceps for seating and dividing tissue having at least one elongated shaft having opposing jaw members at a distal end thereof. The jaw members are movable relative to one another from a first position wherein the jaw members are disposed in spaced relation relative to one another to a second position wherein the jaw members cooperate to grasp tissue therebetween. A drive rod assembly connects the jaw members to a source of electrical energy such that the first jaw member has a first electrical potential and the second jaw member has a second electrical potential. The jaw members, when activated, conduct energy through the tissue held between the jaw members to effect a tissue seal. A handle attaches to the drive rod assembly and, when actuated, imparts movement of the first and second jaw members relative to one another via the drive rod assembly. At least one non-conductive and spaced-apart stop member is disposed on the inner facing surface of one of the jaw members and operates to control the overall gap distance between the opposing seal surfaces of the jaw members when tissue is held therebetween. A trigger mechanically activates a knife for severing the tissue proximate the tissue sealing site.

The present disclosure also relates to a method for sealing and dividing tissue and includes the steps of providing an endoscopic bipolar forceps which includes an elongated shaft having opposing jaw members at a distal end thereof which cooperate to grasp tissue therebetween, at least one non-conductive and spaced-apart stop member disposed on an inner facing surface of at least one of the jaw members which controls the distance between the jaw members when tissue is held therebetween, and a knife.

The method further includes the steps of: connecting the jaw members to a source of electrical energy; actuating the jaw members to grasp tissue between opposing jaw members; conducting energy to the jaw members to through tissue held therebetween to effect a seal; and actuating the knife to sever tissue proximate the seal.

Preferably, at least one of the jaw members of the providing step includes an electrically conductive surface having a longitudinally-oriented channel defined therein which facilitates actuation of the knife in a longitudinally reciprocating fashion within the channel for severing the tissue.

BRIEF DESCRIPTION OF THE DRAWINGS

Various embodiments of the subject instrument are described herein with reference to the drawings wherein:

FIGS. 6A-6F show various configurations for the stop members on the inner facing surface of one of the jaw members;

DETAILED DESCRIPTION

Figure 1:
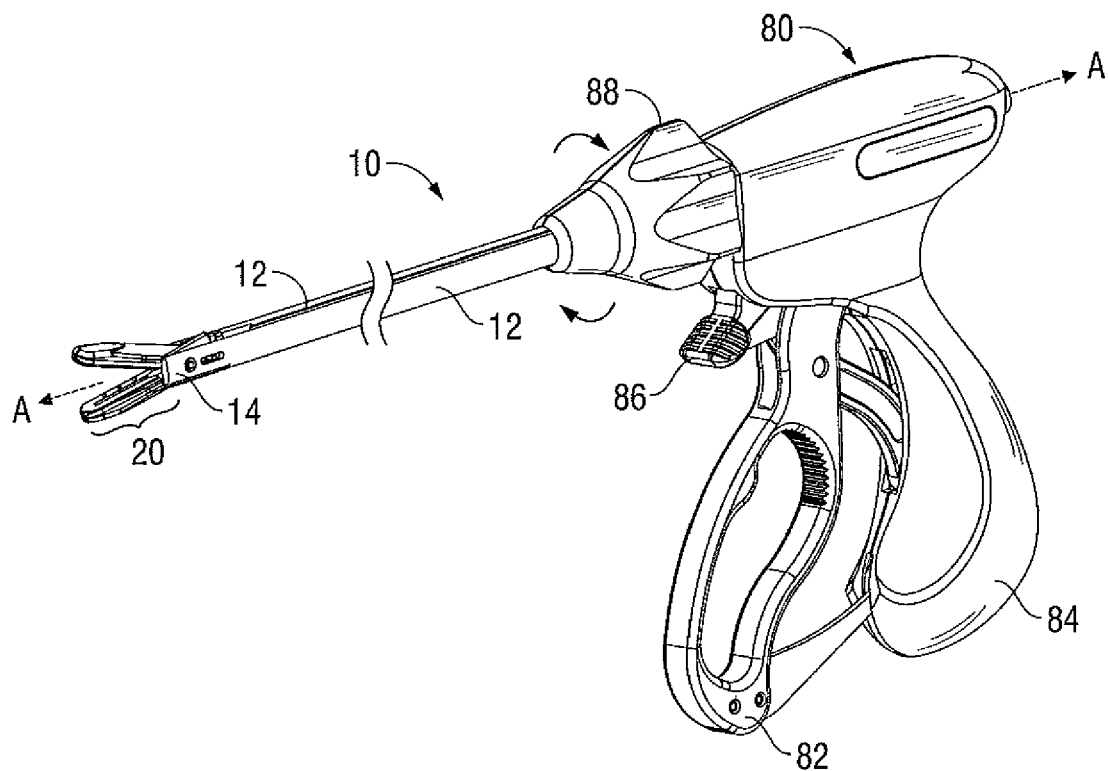
FIG. 1 is a perspective view of an endoscopic forceps showing a handle and an end effector according to the present disclosure.

Referring now to FIGS. 1-5, one embodiment of an endoscopic bipolar forceps 10 is shown for use with various surgical procedures and includes a housing and handle assembly 80 having an end effector assembly 20 attached thereto. More particularly, forceps 10 includes a shaft 12 which has a distal end 14 dimensioned to mechanically engage with the end effector assembly 20 and a proximal end 16 which mechanically engages the housing and handle assembly 80. In the drawings and in the descriptions which follow, the term "proximal", as is traditional, will refer to the end of the forceps 10 which is closer to the user, while the term "distal" will refer to the end which is further from the user.

The end effector assembly 20 is attached to the distal end 14 of shaft 12 and includes a pair of opposing jaw members 22 and 24. Preferably, housing and handle assembly 80 is attached to the proximal end 16 of shaft 12 and includes internally-disposed activating mechanisms, e.g., a movable handle 82 and a drive assembly 70, which mechanically cooperate to impart movement of the jaw members 22 and 24 from an open position wherein the jaw members 22 and 24 are disposed in spaced relation relative to one another, to a clamping or closed position wherein the jaw members 22 and 24 cooperate to grasp tissue 150 (FIG. 7) therebetween.

It is envisioned that the forceps 10 may be designed such that it is fully or partially disposable depending upon a particular purpose or to achieve a particular result. For example, end effector assembly 20 may be selectively and releasably engageable with the distal end 14 of the shaft 12 and/or the proximal end 16 of the shaft 12 may be selectively and releasably engageable with the housing and handle assembly 80. In either of these two instances, the forceps 10 would be considered "partially disposable", i.e., a new or different end effector assembly 20 (or end effector assembly 20 and shaft 12) selectively replaces the old end effector assembly 20 as needed.

Figure 2:
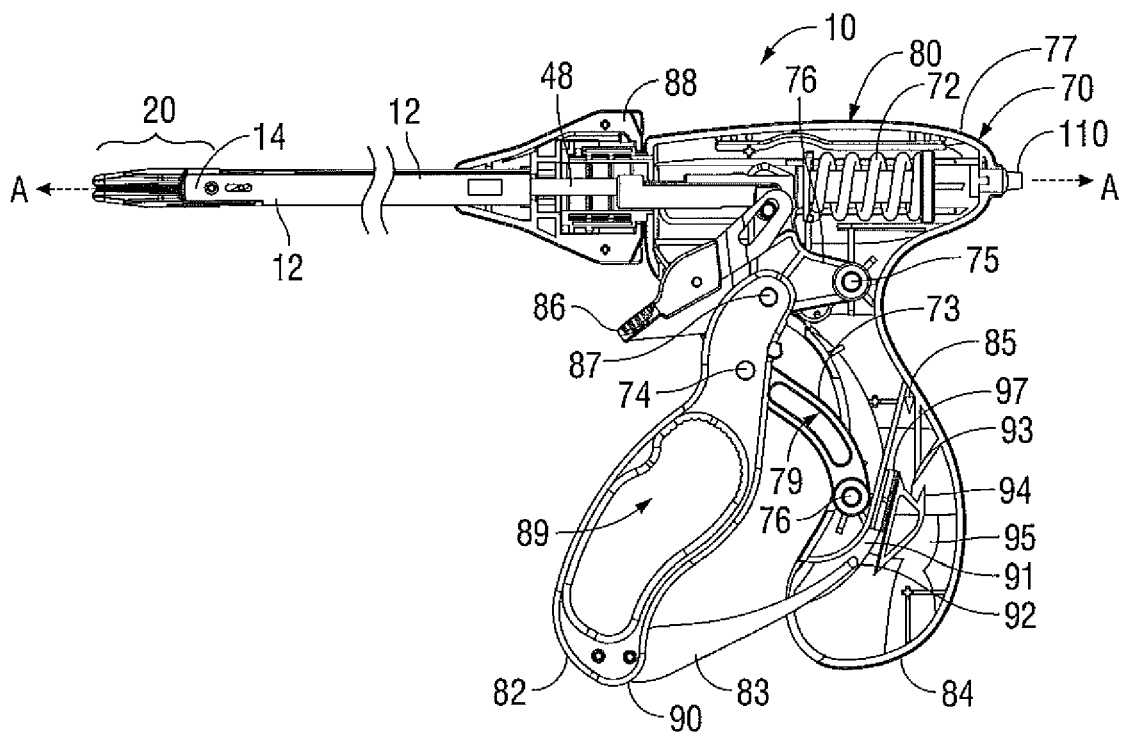
FIG. 2 is a partial cross-section of the forceps of FIG. 1 showing the internal working components of the handle and showing the end effector in a closed configuration.
Figure 3:
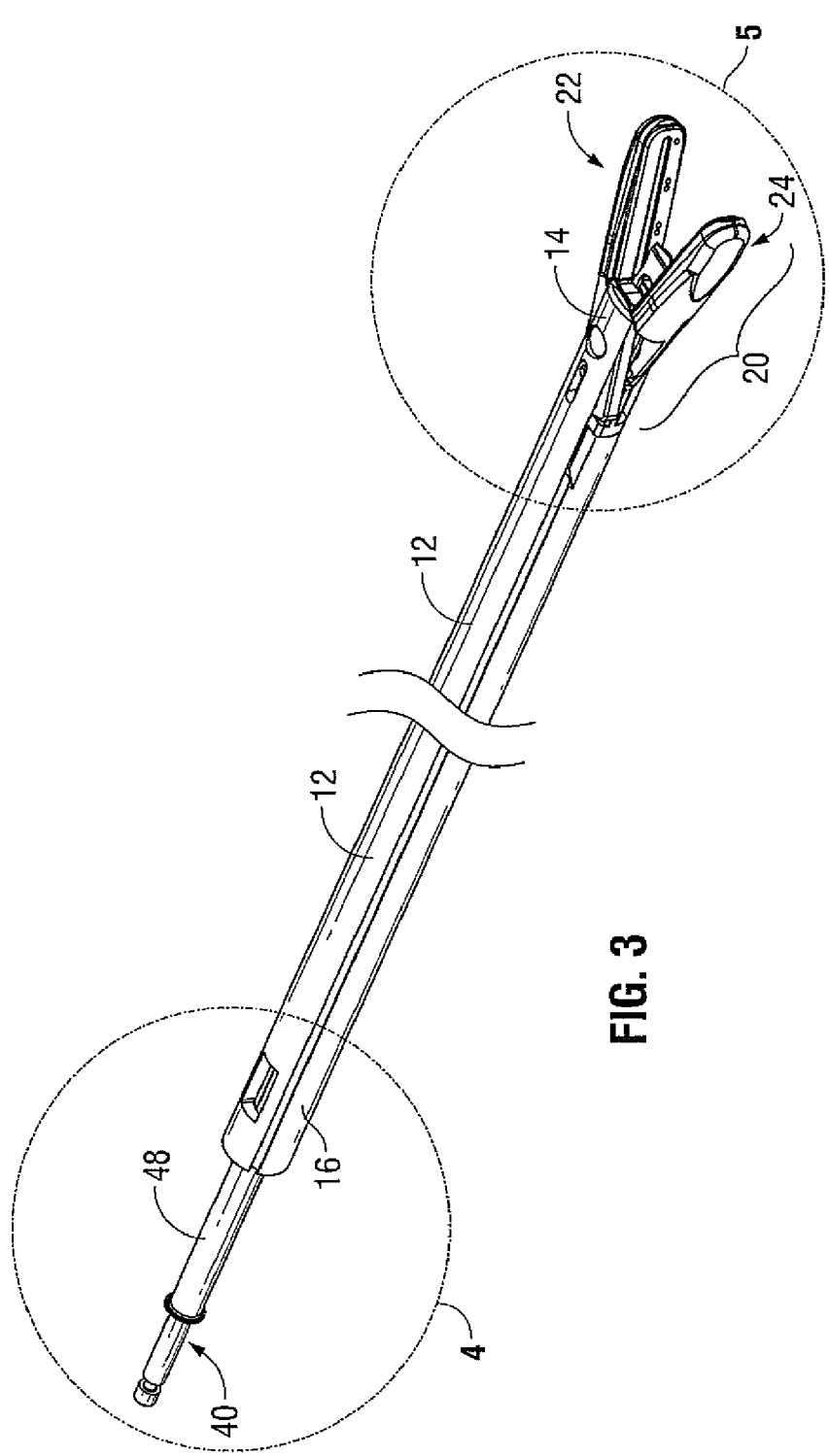
FIG. 3 is an enlarged, perspective view of the end effector assembly shown in open configuration.
Figure 4:
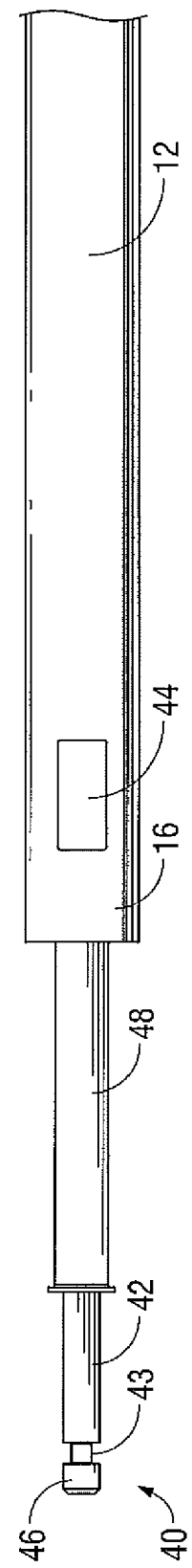
FIG. 4 is a greatly enlarged, side view of a proximal end of the end effector of FIG. 3.

FIGS. 1 and 2 show the operating elements and the internal-working components of the housing and handle assembly 80 which for the purposes of the present disclosure are generally described herein. The specific functions and operative relationships of these elements and the various internal-working components are described in more detail in commonly assigned, co-pending application U.S. Serial No. PCT/US01/11340, entitled "VESSEL SEALER AND DIVIDER" by Dycus et al. which is being filed concurrently herewith and which is hereby incorporated by reference herein in its entirety.

As best shown in FIG. 2, housing and handle assembly 80 includes movable handle 82 and a fixed handle 84. The movable handle 82 includes an aperture 89 defined therethrough which enables a user to grasp and move the handle 82 relative to the fixed handle 84. Movable handle 82 is selectively moveable about a pivot 87 from a first position relative to fixed handle 84 to a second position in closer proximity to the fixed handle 84 which, as explained below, imparts relative movement of the jaw members 22 and 24 relative to one another.

More particularly, housing and handle assembly 80 houses a drive assembly 70 which cooperates with the movable handle 82 to impart movement of the jaw members 22 and 24 from an open position wherein the jaw members 22 and 24 are disposed in spaced relation relative to one another, to a clamping or closed position wherein the jaw members 22 and 24 cooperate to grasp tissue 150 (FIG. 7) therebetween. The general operating parameters of the drive assembly 70 and the internal-working components of the same are explained in a more generalized fashion below but are explained in specific detail in the above-mentioned commonly assigned, co-pending "VESSEL SEALER AND DIVIDER" application. For the purposes of the present disclosure, the housing and handle assembly 80 can generally be characterized as a four-bar mechanical linkage composed of the following elements: movable handle 82, a link 73, a cam-like link 76 and a base link embodied by fixed pivot points 75 and 76. Movement of the handle 82 activates the four-bar linkage which, in turn, actuates the drive assembly 70 for imparting movement of the opposing jaw members 22 and 24 relative to one another to grasp tissue 150 therebetween. It is envisioned that employing a four-bar mechanical linkage will enable the user to gain a significant mechanical advantage when compressing the jaw members 22 and 24 against the tissue 150 as explained in further detail below with respect the generally disclosed operating parameters of the drive assembly 70.

Preferably, fixed handle 84 includes a channel 85 defined therein which is dimensioned to receive a flange 83 which extends proximally from movable handle 82. Preferably, flange 83 includes a fixed end 90 which is affixed to movable handle 82 and a free end 92 which is dimensioned for facile reception within channel 85 of handle 84. It is envisioned that flange 83 may be dimensioned to allow a user to selectively, progressively and incrementally move jaw members 22 and 24 relative to one another from the open to closed positions. For example, it is also contemplated that flange 83 may include a ratchet-like interface which lockingly engages the movable handle 82 and, therefore, jaw members 22 and 24 at selective, incremental positions relative to one another depending upon a particular purpose. Other mechanisms may also be employed to control and/or limit the movement of handle 82 relative to handle 84 (and jaw members 22 and 24) such as, e.g., hydraulic, semi-hydraulic and/or gearing systems.

As can be appreciated by the present disclosure and as explained in more detail with respect to the above-mentioned commonly assigned, co-pending "VESSEL SEALER AND DIVIDER" application, channel 85 of fixed handle 84 includes an entrance pathway 91 and an exit pathway 95 for reciprocation of flange 83. As best shown in FIG. 2, as handle 82 moves in a generally pivoting fashion towards fixed handle 84 about pivot 87, link 73 rotates about a guide pin 74 disposed within handle 82. As a result, link 73 rotates proximally about a pivot 76. As can be appreciated, the pivoting path of handle 82 relative to fixed handle 84 biases cam-like link 76 to rotate about pivot 75 in a generally proximal direction. Movement of the cam-like link 76 imparts movement to the drive assembly 70 as explained below.

As best shown in FIG. 2, upon initial movement of handle 82 towards fixed handle 84, the free end 92 of flange 83 moves generally proximally and upwardly along entrance pathway 91 until end 92 passes or mechanically engages a rail member 97 disposed along pathway 91. It is envisioned that rail 97 permits movement of flange 83 proximally until the point where end 92 clears rail 97. Once end 92 clears rail 97, distal movement of the handle 82 and flange 83, i.e., release, is redirected by rail 97 into the exit pathway 95.

More particularly, upon initial release, i.e., a reduction in the closing pressure of handle 82 against handle 84, the handle 82 returns slightly distally towards pathway 91 but is directed towards exit pathway 95. At this point, the release or return pressure between the handles 82 and 84 which is attributable and directly proportional to the release pressure associated with the compression of the drive assembly 70 (explained below) causes the end 92 of flange 83 to settle or lock within a catch basin 93. Handle 82 is now secured in position within handle 84 which, in turn, locks the jaw members 22 and 24 in a closed position against the tissue. The instrument is now positioned for selective application of electrosurgical energy to form the tissue seal 152. Again, the various operating elements and their relevant functions are explained in more detail with respect to the above-mentioned commonly assigned, co-pending "VESSEL SEALER AND DIVIDER" application.

As best shown in FIG. 2, re-initiation or re-grasping of the handle 82 again moves flange 83 generally proximally along the newly re-directed exit path 95 until end 92 clears a lip 94 disposed along exit pathway 95. Once lip 94 is sufficiently cleared, handle 82 and flange 83 are fully and freely releasable from handle 84 along exit pathway 95 upon the reduction of grasping pressure which, in turn, returns the jaw members 22 and 24 to the open, pre-activated position.

As mentioned above, the housing and handle assembly 80 houses a drive assembly 70 which cooperates with the movable handle 82 to impart relative movement of the jaw members 22 and 24 to grasp the tissue 150. The operation of the drive rod assembly 70 and the various working components of the drive assembly 70 are explained in detail in the above-mentioned commonly assigned, co-pending "VESSEL SEALER AND DIVIDER" application.

Generally and for the purposes of the present disclosure, the drive assembly 70 includes a compression spring 72, a drive rod 40 and a compression sleeve 98 (FIG. 2). As best shown in the enlarged view of FIG. 4, the drive rod 40 is telescopically and internally reciprocable within a knife sleeve 48. Movement of the drive rod 40 relative to the knife sleeve 48 imparts movement to the jaw members 22 and 24. A tab member 46 is disposed at a free end 42 of the drive rod 40 which defines a notch 43 between the tab 46 and end 42. The tab 46 and the notch 43 mechanically cooperate with the compression spring 72 to impart movement of the shaft 40 relative to the knife sleeve 48 which, in turn, opens and closes the jaw members 22 and 24 about the tissue 150.

As explained above, movement of the handle assembly 80 via the four-bar linkage, ultimately causes cam-like link 76 to rotate generally clockwise about pivot 75 (i.e. proximally) which, in turn, compresses spring 72 proximally against a flange 77 disposed within the tipper portion of the fixed handle 84. Movement of the spring 72, in turn, moves the drive rod 40 relative to the knife sleeve 48 which moves the opposing jaw members 22 and 24 relative to one another. As can be appreciated, the significant mechanical advantage associated with the four-bar linkage permits facile, consistent and uniform compression of the spring 72 which, in turn, permits facile, consistent and uniform compression of the jaw members 22 and 24 about the tissue 150. Other details and advantages of the four-bar mechanical linkage are more fully discussed with respect to the above-mentioned commonly assigned, co-pending "VESSEL SEALER AND DIVIDER" application.

Once the tissue 150 is grasped between opposing jaw members 22 and 24, electrosurgical energy can be supplied to the jaw members 22 and 24 through an electrosurgical interface 110 disposed within the handle 84. Again these features are explained in more detail with respect to the above-mentioned commonly assigned, co-pending "VESSEL SEALER AND DIVIDER" application.

Figure 5:
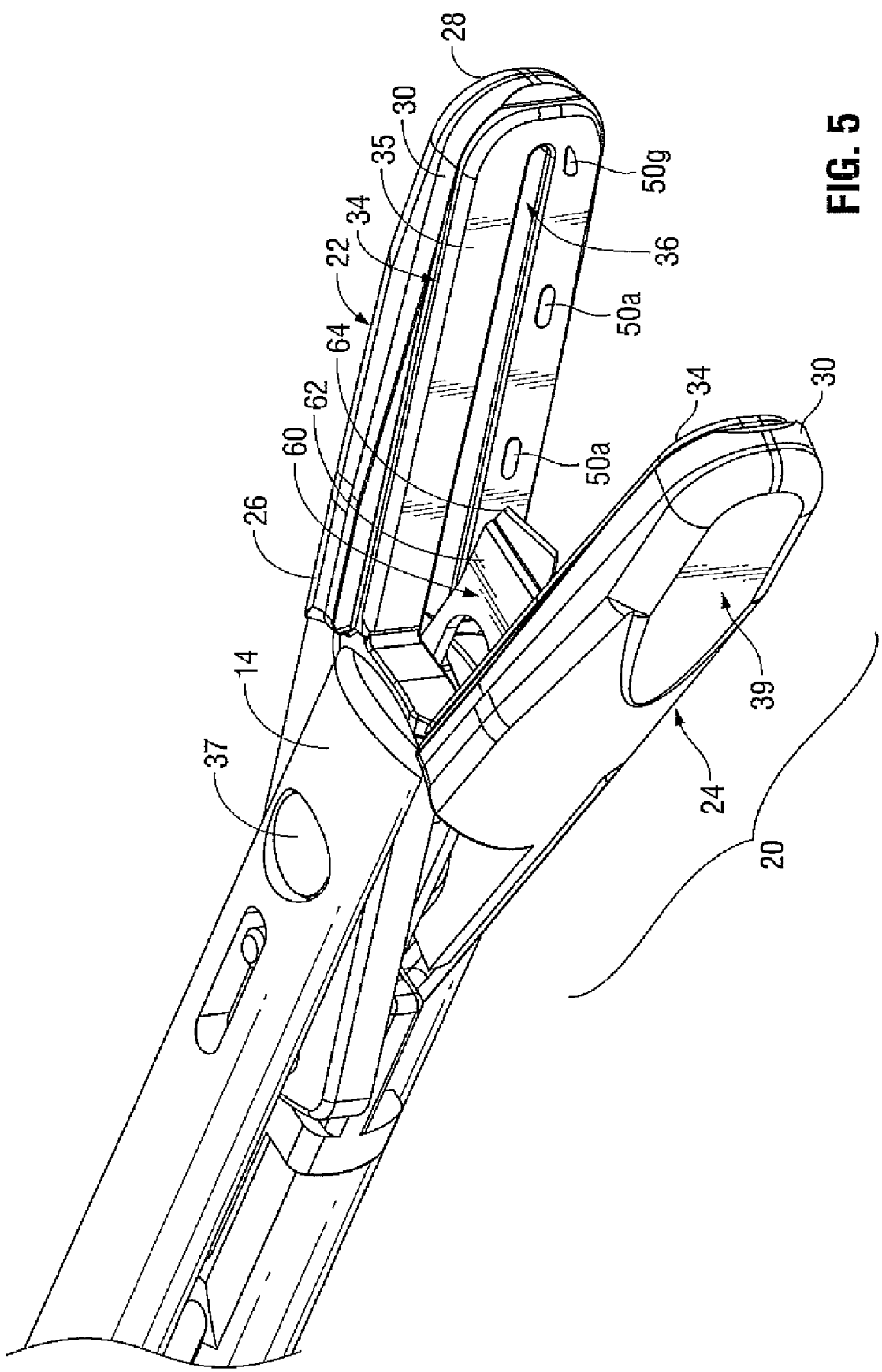
FIG. 5 is a greatly enlarged perspective view of a distal end of the end effector of FIG. 3 showing a knife and a series of stop members disposed along an inner facing surface of a jaw member.
Figure 7:
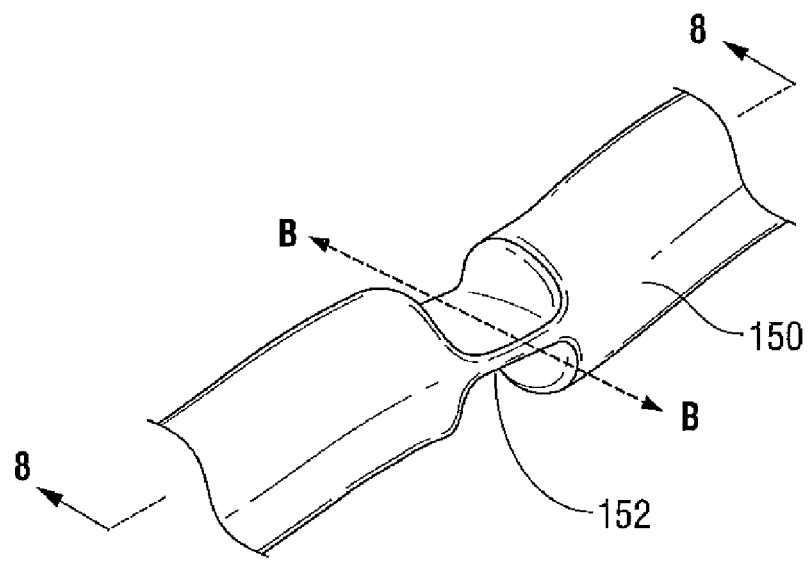
FIG. 7 is an enlarged perspective view of a sealing site of a tubular vessel.
Figure 8:
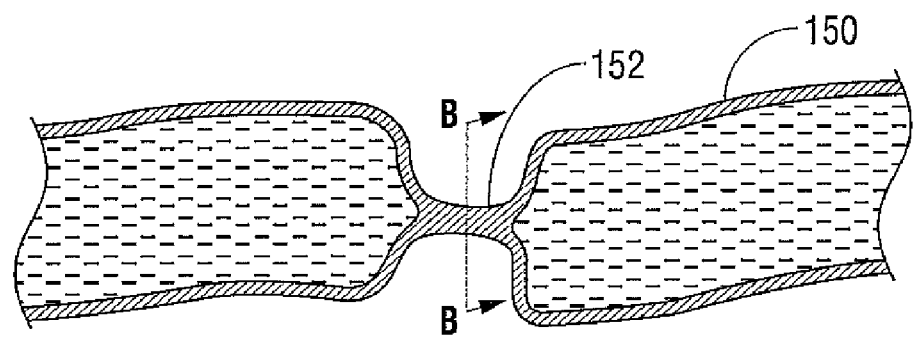
FIG. 8 is a longitudinal cross-section of the sealing site taken along line 8-8 of FIG. 7.
Figure 9:
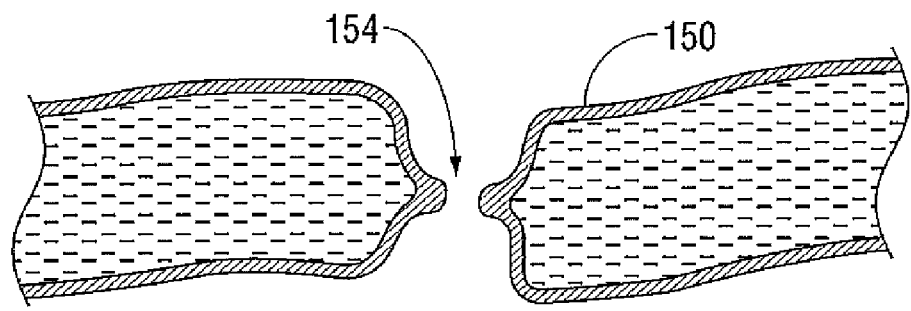
FIG. 9 is a longitudinal cross-section of the sealing site of FIG. 7 after separation of the tubular vessel.

Forceps 10 also includes a trigger 86 which reciprocates the knife sleeve 48 which, in turn, reciprocates a knife 60 disposed within the end effector assembly 20 as explained below (FIG. 5). Once the a tissue seat 152 is formed (FIG. 7), the user can activate the trigger 86 to separate the tissue 150 as shown in FIG. 9 along the tissue seal 152. As can be appreciated, the reciprocating knife 60 allows the user to quickly separate the tissue 150 immediately after sealing without substituting a cutting instrument through the cannula or trocar port (not shown). It is envisioned that the knife 60 also facilitates a more accurate separation of the vessel 150 along an ideal cutting plane "B-B" associated with the newly formed tissue seal 152 (See FIGS. 7-9). Knife 60 preferably includes a sharpened edge 62 for severing the tissue 150 held between the jaw members 22 and 24 at the tissue sealing site 152 (FIG. 7). It is envisioned that knife 60 may also be coupled to the electrosurgical energy source to facilitate separation of the tissue 150 along the tissue seal 152.

Preferably and as explained in more detail with respect to the above-mentioned commonly assigned, co-pending "VESSEL SEALER AND DIVIDER" application, handle assembly 80 may also include a lockout mechanism (not shown) which restricts activation of trigger 86 until the jaw members 22 and 24 are closed and/or substantially closed about tissue 150. For example and as best seen in FIG. 2, exit pathway 95 may be dimensioned such that the trigger 86 is only activatable when flange 83 is disposed in a predetermined or predefined position which provides sufficient clearance for the activation of the trigger 86, e.g., seated within catch basin 93. It is envisioned that configuring the handle assembly 80 in this fashion may reduce the chances of premature activation of the trigger 86 prior to electrosurgical activation and sealing.

A rotating assembly 88 may also be incorporated with forceps 10. Preferably, rotating assembly 88 is mechanically associated with the shaft 12 and the drive assembly 70. As seen best in FIG. 4, the shaft 12 includes an aperture 44 located therein which mechanically interfaces a corresponding detent (not shown) affixed to rotating assembly 88 such that rotational movement of the rotating assembly 88 imparts similar rotational movement to the shaft 12 which, in turn, rotates the end effector assembly 20 about a longitudinal axis "A". These features along with the unique electrical configuration for the transference of electrosurgical energy through the handle assembly 80, the rotating assembly 88 and the drive assembly 70 are described in more detail in the above-mentioned commonly assigned, co-pending "VESSEL SEALER AND DIVIDER" application.

As best seen with respect to FIGS. 3, 5 and 6A-6F, end effector assembly 20 attaches to the distal end 14 of shaft 12. The end effector assembly 20 includes the first jaw member 22, the second jaw member 24 and the reciprocating knife 60 disposed therebetween. The jaw members 22 and 24 are preferably pivotable about a pivot 37 from the open to closed positions upon relative reciprocation, i.e., longitudinal movement of the drive rod 42 as mentioned above. Again, the mechanical and cooperative relationships with respect to the various moving elements of the end effector assembly 20 are further described with respect to the above-mentioned commonly assigned, co-pending "VESSEL SEALER AND DIVIDER" application.

Each of the jaw members includes an electrically conductive sealing surface 35 dispose on inner-facing surface 34 thereof and an insulator 30 disposed on an outer-facing surface 39 thereof. It is envisioned that the electrically conductive surfaces 35 cooperate to seal tissue 150 held therebetween upon the application of electrosurgical energy. The insulators 30 together with the outer, non-conductive surfaces 39 of the jaw members 22 and 24 are preferably dimensioned to limit and/or reduce many of the known undesirable effects related to tissue sealing, e.g., flashover, thermal spread and stray current dissipation.

It is envisioned that the electrically conductive sealing surfaces 35 may also include a pinch trim which facilitates secure engagement of the electrically conductive surface 35 to the insulator 30 and also simplifies the overall manufacturing process. It is envisioned that the electrically conductive sealing surface 35 may also include an outer peripheral edge which has a radius and the insulator 30 meets the electrically conductive sealing surface 35 along an adjoining edge which is generally tangential to the radius and/or meets along the radius. Preferably, at the interface, the electrically conductive surface 35 is raised relative to the insulator 30. These and other envisioned embodiments are discussed in concurrently-filed, co-pending, commonly assigned Application Serial No. PCT/US01/11412 entitled "ELECTROSURGICAL INSTRUMENT WHICH REDUCES COLLATERAL DAMAGE TO ADJACENT TISSUE" by Johnson et al. and concurrently-filed, co-pending, commonly assigned Application Serial No. PCT/US01/11411 entitled "ELECTROSURGICAL INSTRUMENT WHICH IS DESIGNED TO REDUCE THE INCIDENCE OF FLASHOVER" by Johnson et al. The entire contents of both of these applications are hereby incorporated by reference herein.

Preferably, a least one of the electrically conductive surfaces 35 of the jaw members, e.g., 22, includes a longitudinally-oriented channel 36 defined therein which extends from a proximal end 26 to a distal end 28 of the jaw member 22. It is envisioned that the channel 36 facilitates longitudinal reciprocation of the knife 60 along a preferred cutting plane "B-B" to effectively and accurately separate the tissue 150 along the formed tissue seal 152 (See FIGS. 7-9). Preferably and as explained in detail in the above-mentioned commonly assigned, co-pending "VESSEL SEALER AND DIVIDER" application, the jaw members 22 and 24 of the end effector assembly 22 are electrically isolated from one another such that electrosurgical energy can be effectively transferred through the tissue 150 to form seal 152.

As mentioned above, upon movement of the handle 82, the jaw members 22 and 24 close together and grasp tissue 150. At this point flange 83 becomes seated within catch 93 which, together with the mechanical advantage associated with the four-bar mechanism and the spring 70, maintains a proportional axial force on the drive rod 40 which, in turn, maintains a compressive force between opposing jaw members 22 and 24 against the tissue 150. It is envisioned that the end effector assembly 20 may be dimensioned to off-load excessive clamping forces to prevent mechanical failure of certain internal operating elements of the end effector.

By controlling the intensity, frequency and duration of the electrosurgical energy applied to the tissue 150, the user can either cauterize, coagulate/desiccate seal and/or simply reduce or slow bleeding. As mentioned above, two mechanical factors play an important role in determining the resulting thickness of the sealed tissue and effectiveness of the seal, i.e., the pressure applied between opposing jaw members 22 and 24 and the gap distance between the opposing sealing surfaces 35 of the jaw members 22 and 24 during the sealing process. However, thickness of the resulting tissue seal 152 cannot be adequately controlled by force alone. In other words, too much force and the two jaw members 22 and 24 would touch and possibly short resulting in little energy traveling through the tissue 150 thus resulting in a bad tissue seal 152. Too little force and the seal 152 would be too thick.

Applying the correct force is also important for other reasons: to oppose the walls of the vessel; to reduce the tissue impedance to a low enough value that allows enough current through the tissue 150; and to overcome the forces of expansion during tissue heating in addition to contributing towards creating the required end tissue thickness which is an indication of a good seal.

Preferably, the electrically conductive sealing surfaces 35 of the jaw members 22 and 24 are relatively flat to avoid current concentrations at sharp edges and to avoid arcing between high points. In addition and due to the reaction force of the tissue 150 when engaged, jaw members 22 and 24 are preferably manufactured to resist bending. For example and as best seen in FIG. 6A, the jaw members 22 and 24 are preferably tapered along width "W" which is advantageous for two reasons: 1) the taper will apply constant pressure for a constant tissue thickness at parallel; 2) the thicker proximal portion of the jaw members 22 and 24 will resist bending due to the reaction force of the tissue 150.

Figure 6C:
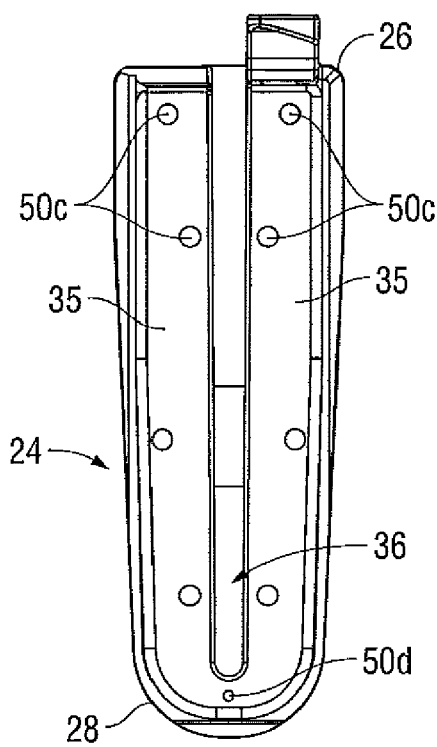
Figure 6D:
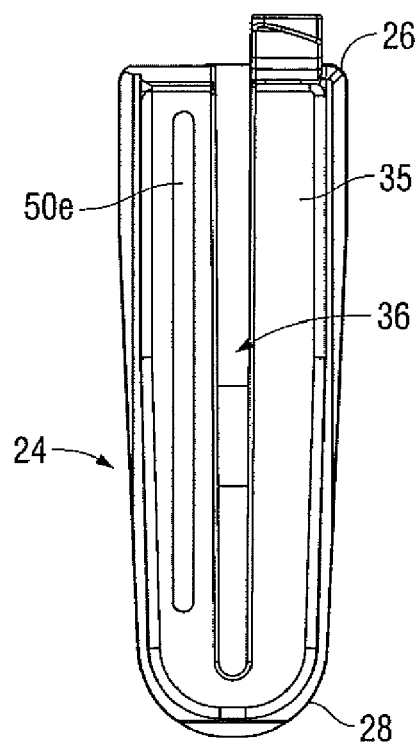
Figure 6E:
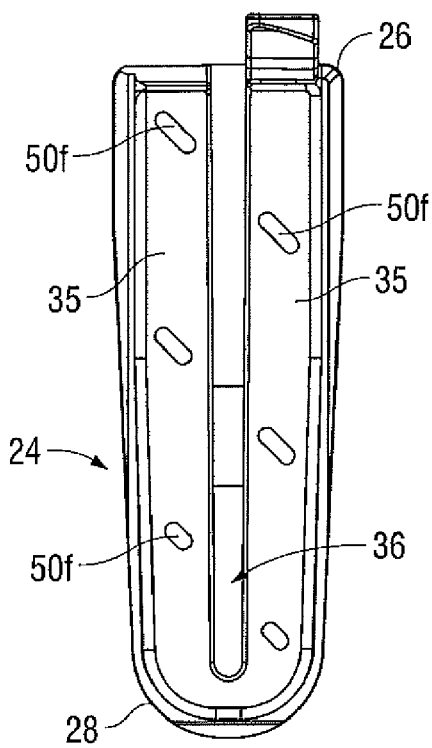
Figure 6F:
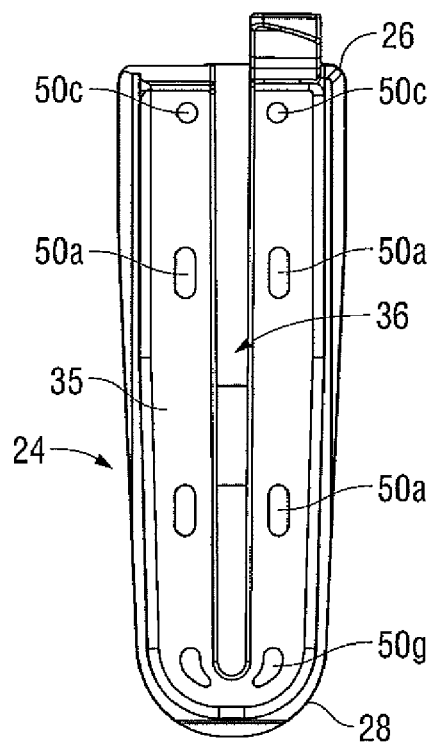

As best seen in FIGS. 5-6F, in order to achieve a desired spacing between the electrically conductive surfaces 35 of the respective jaw members 22 and 24, (i.e., gap distance) and apply a desired force to seal the tissue 150, at least one jaw member 22 and/or 24 includes at least one stop member, e.g., 50*a*, which limits the movement of the two opposing jaw members 22 and 24 relative to one another. Preferably, the stop member, e.g., 50*a*, extends from the sealing surface or tissue contacting surface 35 a predetermined distance according to the specific material properties (e.g., compressive strength, thermal expansion, etc.) to yield a consistent and accurate gap distance during sealing. Preferably, the gap distance between opposing sealing surfaces 35 during sealing ranges from about 0.001 inches to about 0.005 inches and, more preferably, between about 0.002 and about 0.003 inches.

Preferably, stop members 50a-50g are made from an insulative material, e.g., parylene, nylon and/or ceramic and are dimensioned to limit opposing movement of the jaw members 22 and 24 to within the above mentioned gap range. It is envisioned that the stop members 50a-50g may be disposed on one or both of the jaw members 22 and 24 depending upon a particular purpose or to achieve a particular result.

FIGS. 6A-6F show various contemplated configurations of the non-conductive stop members 50a-50g disposed on, along or protruding through the jaw member 24. It is envisioned that one or more stop members, e.g., 50a and 50g, can be positioned on either or both jaw members 22 and 24 depending upon a particular purpose or to achieve a desired result. As can be appreciated by the present disclosure, the various configurations of the stop members 50a-50g are designed to both limit the movement of the tissue 150 prior to and during activation and prevent short circuiting of the jaw members 22 and 24 as the tissue 150 is being compressed.

FIGS. 6A and 6B show one possible configuration of the stop members 50a-50g for controlling the gap distance between opposing seal surfaces 35. More particularly, a pair of longitudinally-oriented tab-like stop members 50a are disposed proximate the center of sealing surface 35 on one side of the knife channel 36 of jaw member 24. A second stop member, e.g., 50b, is disposed at the proximal end 26 of jaw member 24 and a third stop member 50g is disposed at the distal tip 28 of jaw member 24. Preferably, the stop members 50a-50g may be configured in any known geometric or polynomial configuration, e.g., triangular, rectilinear, circular, ovoid, scalloped, etc., depending upon a particular purpose. Moreover, it is contemplated that any combination of different stop members 50a-50g may be assembled along the sealing surfaces 35 to achieve a desired gap distance. It is also envisioned that the stop members may be designed as a raised lip (not shown) which projects from the outer periphery of the jaw member 24.

FIG. 6C shows a first series of circle-like stop members 50c extending from the proximal end 26 to the distal end 28 of jaw member 24 in an alternating, laterally-offset manner relative to one another on one side of the knife channel 36 and a second series of circle-like stop members 50c extending from the proximal end 26 to the distal end 28 of jaw member 24 in an alternating, laterally-offset manner relative to one another on the other side of the knife channel 36. It is envisioned that circle-like stop members 50c are substantially equal in size, however, one or more of the stop members 50c may be dimensioned larger or smaller than the other stop members 50c depending upon a particular purpose or to achieve a desired result.

FIG. 6D shows yet another configuration wherein the stop member is configured as a longitudinally-oriented ridge 50e extending from a proximal end 26 to a distal end 28 of jaw member 82 along one side of knife channel 36. As mentioned above, a second longitudinally-oriented ridge 50e may be disposed on opposing jaw member 22 on the opposite side of knife channel 36 for sealing purposes. FIG. 6E shows a series of elongated tab-like members 50f which are disposed at an angle relative to knife channel 36. FIG. 6F shows yet another configuration wherein different stop members, e.g., 50a, 50c and 50g are disposed atop sealing surface 35 on both sides of the knife channel 36.

Preferably, the non-conductive stop members 50a-50g are molded onto the jaw members 22 and 24 (e.g., overmolding, injection molding, etc.), stamped onto the jaw members 22 and 24 or deposited (e.g., deposition) onto the jaw members 22 and 24. The stop members 50a-50g may also be slideably attached to the jaw members and/or attached to the electrically conductive surfaces 35 in a snap-fit manner. Other techniques involves thermally spraying a ceramic material onto the surface of the jaw member 22 and 24 to form the stop members 50a-50g. Several thermal spraying techniques are contemplated which involve depositing a broad range of heat resistant and insulative materials on the electrically conductive surfaces 35 to create stop members 50a-50g, e.g., High velocity Oxy-fuel deposition, plasma deposition, etc.

It is envisioned that the stop members 50a-50g protrude about 0.001 to about 0.005 inches from the inner-facing surfaces 35 of the jaw members 22 and 24 which, as can be appreciated by the present disclosure, both reduces the possibility of short circuiting between electrically conductive surfaces and enhances the gripping characteristics of the jaw members 22 and 24 during sealing and dividing. Preferably, the stop members 50a-50g protrude about 0.002 inches to about 0.003 inches from the electrically conductive surface 35 which has been determined yield an ideal gap distance for producing effective, uniform and consistent tissue seals.

Alternatively, the stop members 50a-50g can be molded onto the inner-facing surface 35 of one or both jaw members 22 and 24 or, in some cases, it may be preferable to adhere the stop member 50a-50g to the inner facing surfaces 35 of one or both of the jaw members 22 and 24 by any known method of adhesion. Stamping is defined herein to encompass virtually any press operation known in the trade, including but not limited to: blanking, shearing, hot or cold forming, drawing, bending, and coining.

FIGS. 6A-6F show some of the possible configurations of the stop members 50a-50f; however, these configurations are shown by way of example and should not be construed as limiting. Other stop member configurations are also contemplated which may be may be equally effective in reducing the possibility of short circuiting between electrically conductive surfaces 35 and enhancing tissue grip during sealing and dividing.

Further, although it is preferable that the stop members 50a-50g protrude about 0.001 inches to about 0.005 and preferably about 0.002 inches to about 0.003 inches from the inner-facing surfaces 35 of the jaw member 22 and 24, in some cases it may be preferable to have the stop members 50a-50g protrude more or less depending upon a particular purpose. For example, it is contemplated that the type of material used for the stop members 50a-50g and that material's ability to absorb the large compressive closure forces between jaw members 22 and 24 will vary and, therefore, the overall dimensions of the stop members 50a-50g may vary as well to produce the desired gap distance.

In other words, the compressive strength of the material along with the desired or ultimate gap distance required for effective sealing are parameters which are carefully considered when forming the stop members 50a-50g and one material may have to be dimensioned differently from another material to achieve the same gap distance or desired result. For example, the compressive strength of nylon is different from ceramic and, therefore, the nylon material may have to be dimensioned differently, e.g., thicker, to counteract the closing force of the opposing jaw members 22 and 24 and to achieve the same desired gap distance when utilizing a ceramic stop member.

The present disclosure also relates to a method of sealing and dividing tissue and includes the steps of providing an endoscopic bipolar forceps 10 which includes an elongated shaft 12 having opposing jaw members 22 and 24 at a distal end 14 thereof which cooperate to grasp tissue 150 therebetween, at least one non-conductive and spaced-apart stop member 50a-50g disposed on an inner facing surface 35 of at least one of the jaw members, e.g., 24, which controls the distance between the jaw members 22 and 24 when tissue 150 is held therebetween, and a knife 60.

The method further includes the steps of: connecting the jaw members 22 and 24 to a source 110 of electrical energy; actuating the jaw members 22 and 24 to grasp tissue 150 between opposing jaw members 22 and 24; conducting energy to the jaw members 22 and 24 to through tissue 150 held therebetween to effect a seal 152 (FIGS. 7-9); and actuating the knife 60 to sever tissue proximate the seal 152.

Preferably, at least one of the jaw members, e.g., 24, of the providing step includes an electrically conductive surface 35 having a longitudinally-oriented channel 36 defined therein which facilitates actuation of the knife 60 in a longitudinally reciprocating fashion within the channel 36 for severing the tissue 150 proximate the tissue site.

From the foregoing and with reference to the various figure drawings, those skilled in the art will appreciate that certain modifications can also be made to the present disclosure without departing from the scope of the present disclosure. For example, it may be preferable to add other features to the forceps 10, e.g., an articulating assembly to axially displace the end effector assembly 20 relative to the elongated shaft 12.

Moreover, it is contemplated that the presently disclosed forceps may include a disposable end effector assembly which is selectively engageable with at least one portion of the electrosurgical instrument, e.g., shaft 12 and/or handle assembly 80.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of a preferred embodiments. Those skilled in the art will envision other modifications within the scope and spirit of the claims appended hereto.

What is claimed is:

1. An endoscopic bipolar forceps, comprising:
an elongated shaft having opposing jaw members at a distal end thereof, the jaw members including a length and a periphery and movable relative to one another from a first position wherein the jaw members are disposed in spaced relation relative to one another to a second position wherein the jaw members cooperate to grasp tissue therebetween, the jaw members each including respective flat seal surfaces extending along a respective length thereof and adaptable to connect to a source of electrical energy such that the jaw members are capable of conducting energy through tissue held therebetween to effect a tissue seal;
a plurality of non-conductive stop members disposed along the length of at least one of the seal surfaces of at least one of the jaw members such that the plurality of non-conductive stop members are disposed along the same plane on the seal surface with respect to one another, the non-conductive stop members configured to maintain a uniform distance between the jaw members along the length thereof; and a knife disposed in operative communication with at least one of the jaw members and translatable to sever tissue disposed between jaw members.

2. An endoscopic bipolar forceps according to claim 1 wherein the forceps includes at least two non-conductive stop members disposed on the inner facing surface of at least one of the jaw members that extend different heights from the inner facing surface.

3. An endoscopic bipolar forceps according to claim 1 wherein at least one of the jaw members includes an electrically conductive surface having a longitudinally-oriented channel defined therein which facilitates longitudinal translation of the knife for severing tissue.

4. An endoscopic bipolar forceps according to claim 3 wherein at least one non-conductive stop member is disposed on the electrically conductive surface of the jaw member proximate one side of the longitudinally-oriented channel and at least one non-conductive stop member is disposed on the electrically conductive surface of the jaw member proximate another side of the longitudinally-oriented channel.

5. An endoscopic bipolar forceps according to claim 1 wherein the non-conductive stop members are manufactured from the group consisting of: parylene, nylon and ceramic.

6. An endoscopic bipolar forceps according to claim 1 wherein the non-conductive stop members include a series of longitudinally-oriented projections that extend from a proximal end of the jaw member to a distal end of the jaw member.

7. An endoscopic bipolar forceps according to claim 1 wherein the non-conductive stop members include a series of circle-like tabs which extend from a proximal end of the jaw member to a distal end of the jaw member.

8. An endoscopic bipolar forceps according to claim 7 wherein the circle-like tabs are disposed in an alternating, laterally-offset manner relative to one another along a length of the jaw member.

9. An endoscopic bipolar forceps according to claim 1 wherein the non-conductive stop members each protrude about 0.001 inches to about 0.005 inches from the inner facing surface of the jaw member.

10. An endoscopic bipolar forceps according to claim 1 wherein the non-conductive stop members each protrude about 0.002 inches to about 0.003 inches from the inner facing surface of the jaw member.

11. An endoscopic bipolar forceps according to claim 1 wherein the non-conductive stop members are affixed to the jaw member by a molding process.

12. An endoscopic bipolar forceps, comprising:
at least one elongated shaft having opposing jaw members at a distal end thereof, the jaw members movable with respect to the elongated shaft, the jaw members having a length and movable relative to one another from a first position wherein the jaw members are disposed in spaced relation relative to one another to a second position wherein the jaw members cooperate to grasp tissue therebetween;
a drive rod assembly that connects the jaw members to a source of electrical energy such that the first jaw member has a first electrical potential and the second jaw member has a second electrical potential and the jaw members each including respective flat seal surfaces extending along a respective length thereof such that the jaw members are capable of conducting energy through tissue held therebetween to effect a tissue seal;

a handle attached to the drive rod assembly for imparting movement of the first and second jaw members between the first and second positions;

a plurality of non-conductive stop members disposed along the length of at least one of the seal surfaces of least one of the jaw members such that the plurality of non-conductive stop members are disposed along the same plane on the seal surface, the non-conductive stop members configured to maintain a uniform distance between the jaw members along the length thereof; a knife selectively movable to sever tissue along the tissue seal; and a trigger which mechanically activates the knife for severing tissue proximate the tissue seal.

13. An endoscopic bipolar forceps according to claim 12 wherein the jaw members are configured to resist bending.

14. An endoscopic bipolar forceps according to claim 12 wherein the jaw members and the non-conductive stop members are configured such that the jaw members do not contact each other when the jaw members are moved to the second position.

15. An endoscopic bipolar forceps according to claim 12 wherein the jaw members and the non-conductive stop members are configured such that the distance between the jaw members when tissue is held therebetween is between about 0.002 inches and about 0.003 inches.

16. An endoscopic bipolar forceps according to claim 12 wherein the non-conductive stop members include a first pair of non-conductive stop members each being disposed a first distance from the inner facing surface of the jaw member and a second pair of non-conductive stop members each being disposed a second distance from the inner facing surface of the jaw member, and wherein the first distance is not equal to the second distance.

17. An endoscopic bipolar forceps according to claim 12 wherein the non-conductive stop members include at least one pair of non-conductive stop members arranged transversely atop at least one of the inner facing surfaces of one of the jaw members and a non-conductive stop member disposed at a distal tip of at least one of the jaw members.

18. An endoscopic bipolar forceps according to claim 12 wherein the distance between clamped jaw members is uniform along the length of the jaw members.

* * * * *